(12) United States Patent
Tripoli

(10) Patent No.: US 8,494,880 B2
(45) Date of Patent: Jul. 23, 2013

(54) INTERACTIVE PATIENT MEDICATION LIST

(75) Inventor: Louis Christopher Tripoli, Ramona, CA (US)

(73) Assignee: MedImpact Healthcare Systems, Inc.

( * ) Notice: Subject to any disclaimer, the term of this patent is extended or adjusted under 35 U.S.C. 154(b) by 204 days.

(21) Appl. No.: 13/011,783

(22) Filed: Jan. 21, 2011

(65) Prior Publication Data

US 2011/0184753 A1  Jul. 28, 2011

Related U.S. Application Data

(60) Provisional application No. 61/297,707, filed on Jan. 22, 2010.

(51) Int. Cl.
*G06Q 10/00* (2012.01)
*G06Q 50/00* (2012.01)

(52) U.S. Cl.
USPC .................................................. 705/3; 705/2

(58) Field of Classification Search
USPC ........................................................ 705/2–3
See application file for complete search history.

(56) References Cited

U.S. PATENT DOCUMENTS

| | | | |
|---|---|---|---|
| 5,737,539 A * | 4/1998 | Edelson et al. .................... | 705/3 |
| 5,845,255 A * | 12/1998 | Mayaud ............................ | 705/3 |
| 5,950,630 A | 9/1999 | Portwood et al. | |
| 6,317,719 B1 | 11/2001 | Schrier et al. | |
| 6,539,281 B2 * | 3/2003 | Wan et al. ..................... | 700/236 |
| 6,757,898 B1 | 6/2004 | Ilsen et al. | |
| 7,072,840 B1 * | 7/2006 | Mayaud ............................ | 705/2 |
| 7,366,675 B1 * | 4/2008 | Walker et al. ..................... | 705/2 |
| 7,483,839 B2 * | 1/2009 | Mayaud ............................ | 705/2 |
| 7,519,540 B2 * | 4/2009 | Mayaud ............................ | 705/2 |
| 7,574,370 B2 * | 8/2009 | Mayaud ............................ | 705/3 |
| 7,606,723 B2 * | 10/2009 | Mayaud ............................ | 705/2 |
| 7,630,908 B1 | 12/2009 | Amrien et al. | |
| 7,712,288 B2 | 5/2010 | Ramasubramanian et al. | |
| 7,801,745 B2 * | 9/2010 | Walker et al. ..................... | 705/2 |
| 8,055,509 B1 * | 11/2011 | Walker et al. ..................... | 705/2 |
| 8,069,056 B2 * | 11/2011 | Walker et al. ..................... | 705/2 |
| 8,249,897 B2 * | 8/2012 | Yamaga et al. .................... | 705/3 |
| 2002/0032582 A1 | 3/2002 | Feeney et al. | |
| 2002/0042725 A1* | 4/2002 | Mayaud ............................ | 705/2 |
| 2002/0042726 A1* | 4/2002 | Mayaud ............................ | 705/2 |
| 2002/0080034 A1 | 6/2002 | Yahalom | |
| 2002/0095314 A1 | 7/2002 | Bodsworth et al. | |
| 2002/0138302 A1 | 9/2002 | Bodnick | |
| 2002/0153411 A1* | 10/2002 | Wan et al. ..................... | 235/375 |

(Continued)

OTHER PUBLICATIONS

Aschenbrenner, et al., "Drug Therapy in Nursing"; Lippincott Williams & Wilkins (2008) 4 pages.

(Continued)

*Primary Examiner* — Michael Fuelling
(74) *Attorney, Agent, or Firm* — Fish & Richardson P.C.

(57) ABSTRACT

Systems, methods and devices for managing patient medication data which include, in one implementation, displaying in a user-interface movable medication containers for medications in a list of medications for a patient, each medication container having a corresponding medication category; displaying a receptacle for organizing the medications, the receptacle having multiple layers having corresponding medication categories in a first dimension, each layer configured to receive one or more medication containers; and receiving a first medication container from the movable medication containers that is dragged into a layer in the first dimension having a corresponding medication category that matches the medication category of the first medication container.

15 Claims, 27 Drawing Sheets

U.S. PATENT DOCUMENTS

| | | | |
|---|---|---|---|
| 2003/0144884 A1* | 7/2003 | Mayaud | 705/3 |
| 2004/0073457 A1 | 4/2004 | Kalies | |
| 2005/0060197 A1* | 3/2005 | Mayaud | 705/2 |
| 2005/0138564 A1 | 6/2005 | Fogg | |
| 2005/0288966 A1 | 12/2005 | Young | |
| 2007/0033073 A1 | 2/2007 | Tajaliawal et al. | |
| 2007/0067186 A1 | 3/2007 | Brenner et al. | |
| 2007/0143141 A1 | 6/2007 | Villasenor et al. | |
| 2007/0143142 A1 | 6/2007 | Villasenor et al. | |
| 2007/0185803 A1 | 8/2007 | Harrison et al. | |
| 2007/0226009 A1 | 9/2007 | Hicks | |
| 2008/0221547 A1* | 9/2008 | Monty | 604/500 |
| 2009/0048864 A1 | 2/2009 | Kozlowski et al. | |
| 2009/0157424 A1 | 6/2009 | Hans | |
| 2010/0106529 A1 | 4/2010 | McCallie et al. | |
| 2010/0161353 A1* | 6/2010 | Mayaud | 705/3 |

OTHER PUBLICATIONS

Harris, et al., "RightRX: Decision Support for the Optimization of Prescribing Practice" Toward the Electronic Patient Record; Orlando, FL (Feb. 1995) 4 pages.

HealthVault, [online] [Retrieved on Jan. 24, 2011]; Retrieved from the Internet URL: http://www.healthvault.com/personal/hv_final_overview_master_02.pdf, 10 pages.

\* cited by examiner

My Medication List

☑

213 – ☐ NAME: Charles Chu  216 – ALLERGIES: Penicillin   221 – 🖨 Print Medication List
223 –   218 – [Add New Allergy]  226 –   229 –

210 –

| Drug Name | Prescriber | No Longer Taking |
|---|---|---|
| CARBAMAZEPINE 200 mg | Dr. Smith | 230 → ☐ |
| CIPROFLOXACIN 500 mg | Dr. Jones | ☐ |
| DETROL LA 4 mg | Dr. Smith | ☐ |
| GLYBURIDE 2.5 mg | Dr. Smith | ☐ |
| INDOMETHACIN 25 mg | Dr. Smith | ☐ |
| METFORMIN ER 750 mg | Dr. Jones | ☐ |
| METOPROLOL 25 mg | Dr. Jones | ☐ |
| NEXIUM 4 mg | Dr. Smith | ☐ |
| PLAVIX 75 mg | Dr. Jones | ☐ |
| LASIX 40 mg | Dr. Jones | ☐ |
| FUROSEMIDE 40 mg | Unknown | ☐ |
| IBUPROFEN 600 mg | Dr. Adams | ☐ |

254 – NEXIUM
253 – PLAVIX
250 – LASIX
251 – FUROSEMIDE
252 – IBUPROFEN

233 – [Add New Medication]

My Medication List

| | NAME: Charles Chu | ALLERGIES: Penicillin | Print Medication List |
|---|---|---|---|
| | | Add New Allergy | |

| Drug Name | Prescriber | No Longer Taking |
|---|---|---|
| CARBAMAZEPINE 200 mg | Dr. Smith | ☐ |
| CIPROFLOXACIN 500 mg | Dr. Jones | ☐ |
| DETROL LA 4 mg | Dr. Smith | ☐ |
| GLYBURIDE 2.5 mg | Dr. Smith | ☐ |
| INDOMETHACIN 25 mg | Dr. Smith | ☐ |
| METFORMIN ER 750 mg | Dr. Jones | ☐ |
| METOPROLOL 25 mg | Dr. Jones | ☐ |
| NEXIUM 4 mg | Dr. Smith | ☐ |
| PLAVIX 75 mg | Dr. Jones | ☐ |
| LASIX 40 mg | Dr. Jones | ☐ |
| IBUPROFEN 600 mg | Dr. Adams | ☐ |

Add New Medication

My Medication List

☑ NAME: Charles Chu   ALLERGIES: Penicillin   🖨 Print Medication List
                      [Add New Allergy]

| Drug Name | Prescriber | No Longer Taking |
|---|---|---|
| CARBAMAZEPINE 200 mg | Dr. Smith | ☐ |
| CIPROFLOXACIN 500 mg | Dr. Jones | ☐ |
| DETROL LA 4 mg | Dr. Smith | ☐ |
| GLYBURIDE 2.5 mg | Dr. Smith | ☐ |
| INDOMETHACIN 25 mg | Dr. Smith | ☐ |
| METFORMIN ER 750 mg | Dr. Jones | ☐ |
| METOPROLOL 25 mg | Dr. Jones | ☐ |
| NEXIUM 4 mg | Dr. Smith | ☐ |
| PLAVIX 75 mg | Dr. Jones | ☐ |
| FUROSEMIDE 40 mg | Unkown | ☐ |
| IBUPROFEN 600 mg | Dr. Adams | ☐ |

MEDICATIONS REMOVED FROM YOUR LIST

| LASIX 40 mg | Removed by Dr. Jones | [Physician's Notes] | [Confirm You've Discontinued] |
|---|---|---|---|

*FIG. 3e*

My Medication List

☑ NAME: Charles Chu   ALLERGIES: Penicillin   [Add New Allergy]   ≡ Print Medication List

| Drug Name | Prescriber | No Longer Taking |
|---|---|---|

The Medication Management Application has identified that the following medications may conflict.

| Drug Name |
|---|
| NEXIUM 4 mg |
| PLAVIX 75 mg |

[More Information]

[Request Resolution From Physician]

| PLAVIX 75 mg | Dr. Jones | ☐ |
| LASIX 40 mg | Dr. Jones | ☐ |
| FUROSEMIDE 40 mg | Unkown | ☐ |
| IBUPROFEN 600 mg | Dr. Adams | ☐ |

[Add New Medication]

*FIG. 4a*

My Medication List

☑ NAME: Charles Chu    ALLERGIES: Penicillin    🖨 Print Medication List
   [Add New Allergy]

| Drug Name | Prescriber | No Longer Taking |
|---|---|---|
| CARBAMAZEPINE 200 mg | Dr. Smith | ☐ |
| CIPROFLOXACIN 500 mg | Dr. Jones | ☐ |
| DETROL LA 4 mg | Dr. Smith | ☐ |
| GLYBURIDE 2.5 mg | Dr. Smith | ☐ |
| INDOMETHACIN 25 mg | Dr. Smith | ☐ |
| METFORMIN ER 750 mg | Dr. Jones | ☐ |
| METOPROLOL 25 mg | Dr. Jones | ☐ |
| NEXIUM 4 mg | Dr. Smith | ☐ |
| LASIX 40 mg | Dr. Jones | ☐ |
| FUROSEMIDE 40 mg | Unkown | ☐ |
| IBUPROFEN 600 mg | Dr. Adams | ☐ |

[Add New Medication]

MEDICATIONS REMOVED FROM YOUR LIST

| PLAVIX 75 mg | Removed by Dr. Jones | [Physician's Notes] | [Confirm You've Discontinued] |

My Medication List

☑ NAME: Charles Chu    ALLERGIES: Penicillin

[Add New Allergy]    ~210

[Print Medication List]

| Drug Name | Prescriber | No Longer Taking |
|---|---|---|
| CARBAMAZEPINE 200 mg | Dr. Smith | ☐ |
| CIPROFLOXACIN 500 mg | Dr. Jones | ☐ |
| DETROL LA 4 mg | Dr. Smith | ☐ |
| GLYBURIDE 2.5 mg | Dr. Smith | ☐ |
| INDOMETHACIN 25 mg | Dr. Smith | ☐ |
| METFORMIN ER 750 mg | Dr. Jones | ☐ |
| METOPROLOL 25 mg | Dr. Jones | ☐ |
| NEXIUM 4 mg | Dr. Smith | ☐ |
| PLAVIX 75 mg | Dr. Jones | ☐ |
| LASIX 40 mg | Dr. Jones | ☐ |
| FUROSEMIDE 40 mg | Unkown | ☐ |
| IBUPROFEN 600 mg | Dr. Adams | ☐ |
| LIPITOR 10 mg | | ☐ |

621 — A similar medication may be available which could save you up to $30 a month. Click here ⦿ to send a notification to your physician requesting him to consider this alternative for you. Click here ⦿ for more information.

My Medication List

| | | |
|---|---|---|
| NAME: Charles Chu | ALLERGIES: Penicillin  [Add New Allergy] | Print Medication List |

| Drug Name | Prescriber | No Longer Taking |
|---|---|---|
| CARBAMAZEPINE 200 mg | Dr. Smith | ☐ |
| CIPROFLOXACIN 500 mg | Dr. Jones | ☐ |
| DETROL LA 4 mg | Dr. Smith | ☐ |
| GLYBURIDE 2.5 mg | Dr. Smith | ☐ |
| INDOMETHACIN 25 mg | Dr. Smith | ☐ |
| METFORMIN ER 750 mg | Dr. Jones | ☐ |
| METOPROLOL 25 mg | Dr. Jones | ☐ |
| NEXIUM 4 mg | Dr. Smith | ☐ |
| PLAVIX 75 mg | Dr. Jones | ☐ |
| LASIX 40 mg | Dr. Jones | ☐ |
| FUROSEMIDE 40 mg | Unkown | ☐ |
| IBUPROFEN 600 mg | Dr. Adams | ☐ |
| [$] LIPITOR 10 mg | Dr. Adams | ☐ |

[Add New Medication]

The following prescriptions are now available at XYZ Pharmacy to replace your prescription for LIPITOR 10 mg

| Drug Name | Prescriber | Savings |
|---|---|---|
| SIMVASTATIN 10 mg | Dr. Adams | $30/month |

*FIG. 6b*

My Medication List

NAME: Charles Chu    ALLERGIES: Penicillin    Print Medication List

Add New Allergy

| Drug Name | Prescriber | No Longer Taking |
|---|---|---|
| CARBAMAZEPINE 200 mg | Dr. Smith | ☐ |
| CIPROFLOXACIN 500 mg | Dr. Jones | ☐ |
| DETROL LA 4 mg | Dr. Smith | ☐ |
| GLYBURIDE 2.5 mg | Dr. Smith | ☐ |
| INDOMETHACIN 25 mg | Dr. Smith | ☐ |
| METFORMIN ER 750 mg | Dr. Jones | ☐ |
| METOPROLOL 25 mg | Dr. Jones | ☐ |
| NEXIUM 4 mg | Dr. Smith | ☐ |
| PLAVIX 75 mg | Dr. Jones | ☐ |
| LASIX 40 mg | Dr. Jones | ☐ |
| FUROSEMIDE 40 mg | Unknown | ☐ |
| IBUPROFEN 600 mg | Dr. Adams | ☐ |
| SIMVASTATIN 10 mg | Dr. Adams | ☐ |

Add New Medication

MEDICATIONS REMOVED FROM YOUR LIST

LIPITOR 10 mg    Removed by Dr. Jones    Replaced by SIMVASTATIN    [Physician's Notes]    [Confirm You've Discontinued]

*FIG. 6c*

Personal Health Report Card

Maintenance Medication History

| Drug Name & Strength | Rx Dispensed Dates and Duration | Refill Rating |
|---|---|---|
| | Jan 2011  Feb 2011  Mar 2011  Apr 2011  May 2011  Jun 2011 | |

Brain & Pain

| SERTRALINE HCL 100 MG TA | (timeline) | ☆☆☆☆☆ |
| CLOZAPINE 100 MG TABLET | (timeline) | ☆☆☆☆ |
| GEODON 80 MG CAPSULE | (timeline) | |

Heart & Lungs

| METOPROLOL TARTRATE 25 | (timeline) | ☆☆☆ |
| [$] CARVEDILOL 3.125 MG TABL | (timeline) | ☆☆☆☆☆ |
| LISINOPRIL 5 MG TABL | (timeline) | ☆☆☆☆ |

△ Retail refill —— Retail Rx duration  ■ Mail-order refill —— Mail-order Rx duration  [$] Savings Opportunity ☆☆☆☆☆ Great! Keep up the good work.     ☆☆ Discuss at your next visit.
☆☆☆ Good. Continue to monitor.          ☆ Consult with your physician immediately.

Non-Maintenance Medication History

| Drug Name & Strength | Rx Dispensed Dates and Duration |
|---|---|
| | Jan 2011  Feb 2011  Mar 2011  Apr 2011  May 2011  Jun 2011 |

Brain & Pain

| HYDROCODONE-APAP 5-500 | (timeline) |
| MORPHINE SULFER 15 MG T | (timeline) |
| OXYCODONE-APAP 5-325 M | (timeline) |

Infections (Drugs for Bugs)

| SULFAMETHOXAZOLE-TMP | (timeline) |

△ Retail refill —— Retail Rx duration  ■ Mail-order refill —— Mail-order Rx duration  [$] Savings Opportunity

PROBLEMS

Polypharmacy

| Prescriptions = 26 | Prescribers = 7 | Pharmacies = 1 |

Polypharmacy is viewed when someone is taking many medications at the same time. Your records indicate the highest risk of unwanted side effects. Be sure to discuss with your doctor or pharmacist if you haven't already done so.

| Medication Alerts | Drug Name | Description | Rating |
|---|---|---|---|
| THERAPEUTIC DUPLICATION | MORPHINE SULFER-15 MG TABLET<br>HYDROCODONE-APAP 5-325 TABLET | These medications treat the same condition, contact your doctor or pharmacist. Click here to notify doctor ● | △ |

FIG. 7

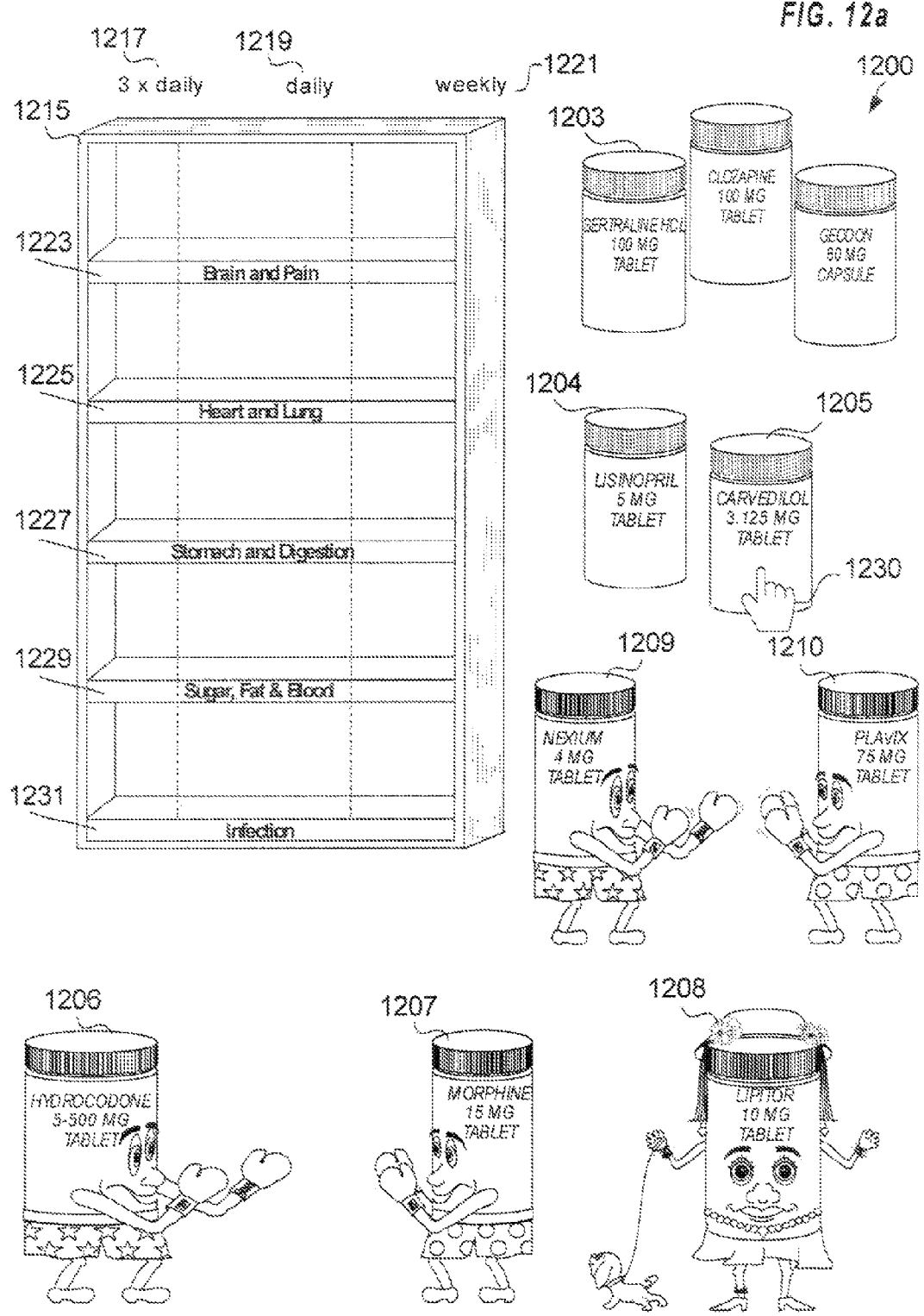

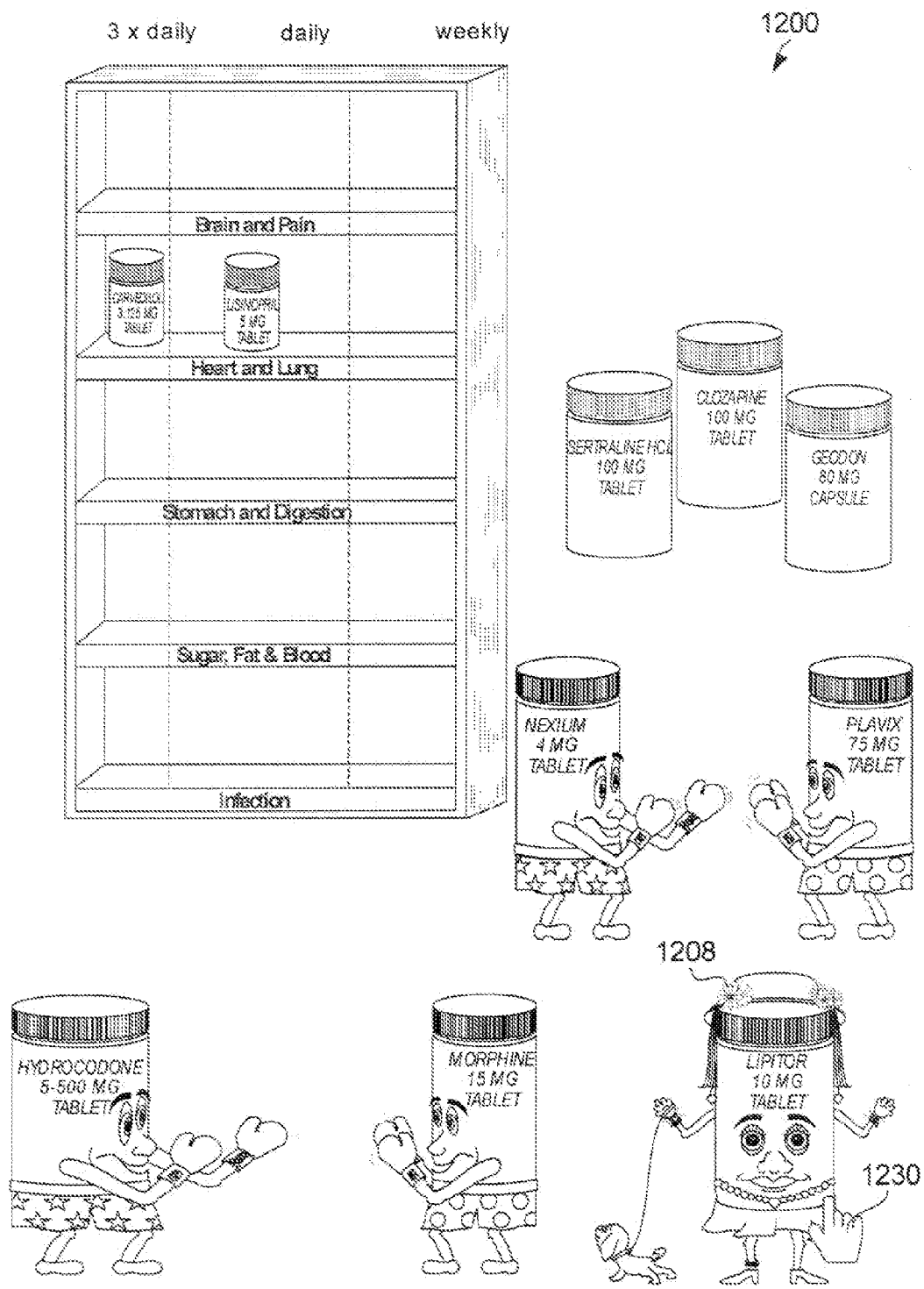

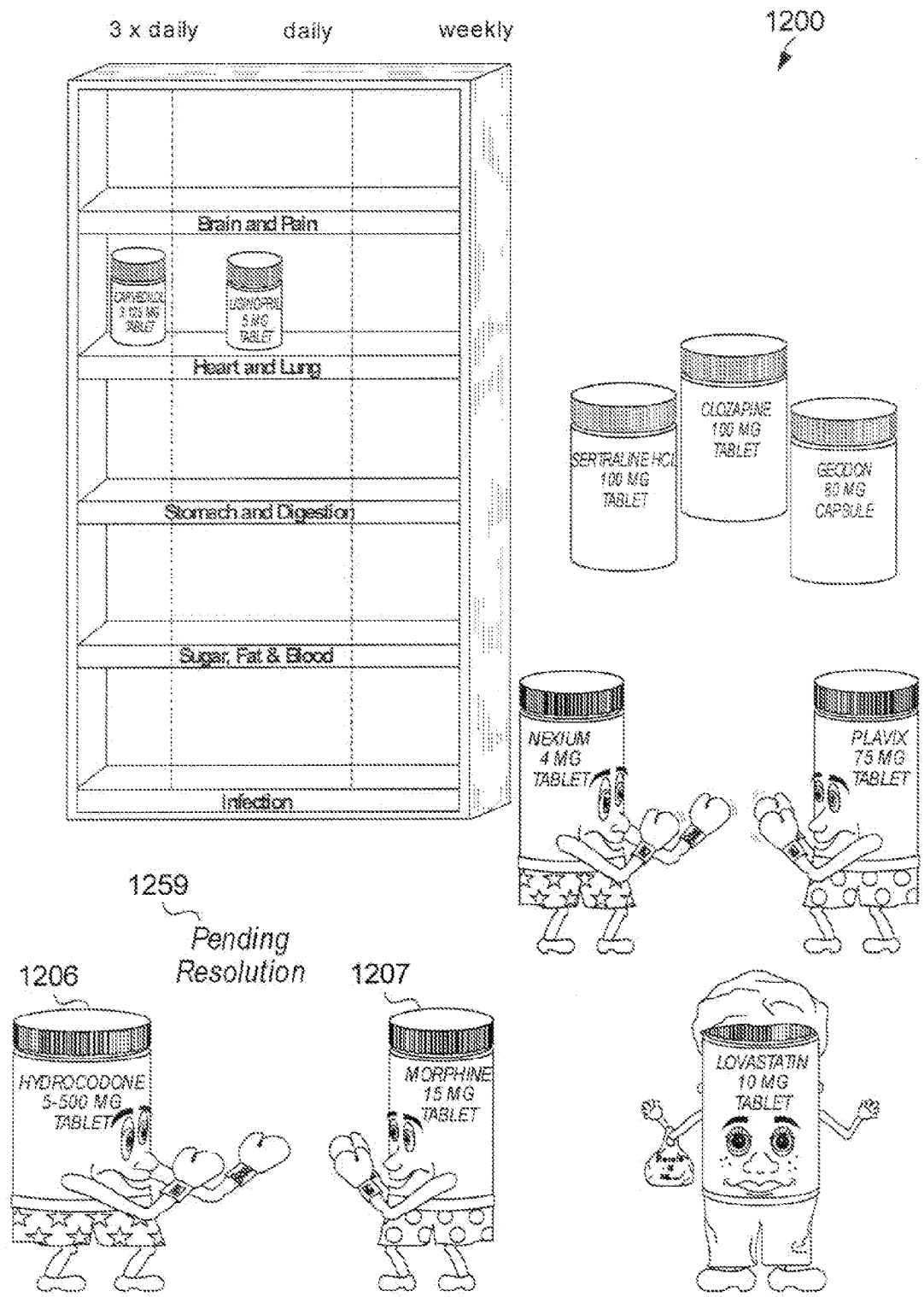

INTERACTIVE PATIENT MEDICATION LIST

This application claims priority to U.S. Provisional Application 61/297,707, filed Jan. 22, 2010. The disclosure of the prior application is considered part of (and is incorporated by reference in) the disclosure of this application.

TECHNICAL FIELD

This patent document relates computer-based systems and techniques for managing patient medication data, including reconciling and maintaining patient medication lists.

BACKGROUND

A patient can receive various medical treatments to treat a disease or a medical condition. A medical treatment can include prescribing a medication that must be taken by the patient for one or more medical conditions in prescribed doses at certain intervals over the course of a treatment period. For some patients, the complexity of their medication list can increase overtime. For example, during the course of treatment, the medical professional can change a prescribed medication with a replacement medication, add one or more additional medications, or change the dosing of a currently prescribed medication. Also, other medical professionals caring for the patient can prescribe other medications for treating other conditions. The number of medications a patient has for active and inactive prescriptions can accumulate overtime. Additionally, the patient can also purchase over-the-counter medications. Under these and other circumstances, managing patient's medication data can become difficult.

SUMMARY

It can become increasingly difficult for a patient to determine what medications the patient should be taking as the number of medications accumulates from multiple prescriptions from multiple prescribers over the course of time. Some medications a patient has can be left over from a discontinued prescription. The patient may also be taking over-the-counter medications which can further complicate the medication regimen the patient is supposed to be on. Also, as the number of medications a patient takes increases, the higher the likelihood for problems to appear in the patient's medication list.

Problems can include, for example, duplicate medications, similar medications, and drug conflicts. In addition, patients may not fill or refill medications as prescribed. Duplicate medications include medications that are the same generic medication, same dose, same form, and same route of administration but have different fill locations or fill dates. Similar medications can include medications that are the same generic medication but one or more of the dose, form, and route of administration are different. Therapeutic duplicates include medications that are in the same therapeutic drug class and are used to treat the same condition. Conflicts can include for example incompatible medications on the list (e.g. "drug-to-drug" interactions), drug-genomic conflicts (e.g. conflicts between a drug and a patient's genetic make-up), drug-physiology or drug-to-disease conflicts (e.g. conflicts between a drug and a patient's physiology or disease state), drug allergies etc.

This patent document describes systems, methods, and techniques for presenting a medication list to a patient and for maintaining updates to the medication list. For example, the systems, methods, and techniques disclosed can determine an up-to-date medication list for the patient. The systems, methods, and techniques can also allow a patient to keep a patient medication list updated over time and to address problems that arise as medications are changed or added.

In some implementations, a computer-based system can be configured to obtain medication data can from multiple sources. A list of medications can be compiled from the medication data from multiple sources. Multiple entries for identical medications—e.g., entries for the exact same bottle of prescribed medication—can be identified and consolidated by the system. The consolidated medication list can be presented to the patient. In some examples, the medication data from multiple sources can be insufficient to determine whether multiple medication entries in that data are identical medications. In such cases, the system can receive user input confirming whether the medications for said entries are identical medications or whether the patient is (or was) taking both medications.

One or more problems in the medication list can be determined and presented to the patient along with the medication list. The patient can provide input to the system to resolve the problem. For example, the patient can provide patient input indicating that a medication involved in the problem is no longer being taken. If the patient is currently taking all of the one or more medications involved in the problem, the patient can initiate a request via the system to a health care professional to resolve the problem.

The health care professional can resolve the problem via the system by indicating that one or more medications in the patient medication list should be discontinued. In some examples, the health care professional can also issue a new prescription for a new medication to replace a medication on the list. The physician can also update a prescription with a new dosage and frequency of administration. The physician can determine that it is appropriate for the patient to be taking both medications at the dose and schedule originally prescribed. The physician can give the patient specific instructions on how to take the medications, for example, not to take both medications within two hours of each other. Additionally, the physician can provide special precautionary information for the patient, such as specific side effects or adverse effects to watch for, and/or under what circumstances to contact the physician. The patient list can be updated automatically based on the health care professional's input. In some examples, new medication data, such as prescription data and/or claims data, can be obtained from one or more of the multiple sources, consolidated, and added to the patient list.

In some implementations, potential cost savings can be determined by the system and presented to the patient on the patient's medication list. The cost savings can be determined based on the patient's medication plan using data from, for example, the patient health care plan or from a pharmacy benefit management service. The patient can select the potential cost savings, and depending upon the type of potential cost savings, a request can be generated and sent to a health care professional or to the patient's pharmacy for approval or denial of the request. The patient's medication list can be updated according to whether the patient's physician agrees with the request or not. For example, if the request is not fulfilled, the patient's list can be updated by removing the cost savings indicator. Also, the list can include an indication that shows the disagreement with the request and the reason for it. If the request is granted, the medication list can be updated with the cost savings change. When the cost savings requires a new prescription, an indication can be presented to the patient with the patient's medication list that the prescription has been provided to the patient's pharmacy. When the patient receives the filled prescription, the system can obtain medication data, e.g., from the pharmacy and/or from the patient's PBM (e.g. claims data), the list can be updated to include the new prescription. A medication that is replaced by the prescription can be removed from the list.

In some examples, the system can be implemented to award points for using the system to maintain an updated medication list and to incentivize the patient to update the patient's medication list. Points can accumulate as the patient resolves problems or has problems resolved on the list. Points can also accumulate as the patient requests cost savings changes to their medication list. Points can also accumulate as the patient improves and/or maintains good adherence to their medications. The points can be redeemed by the patient for rewards such as for savings on co-payments and/or for other prizes.

The details of one or more embodiments are set forth in the accompanying drawings and the description below. Other features, objects, and advantages of the invention will be apparent from the description and drawings, and from the claims.

DESCRIPTION OF DRAWINGS

FIGS. 2-6c show an example user-interface for presenting an interactive patient medication list.

FIG. 7 shows an example user-interface for displaying a patient medication list in the form of a personal health report card for a patient.

FIGS. 12a-12h show an example of an interactive patient medication list.

Like reference symbols in the various drawings indicate like elements.

DETAILED DESCRIPTION

Figure 1:
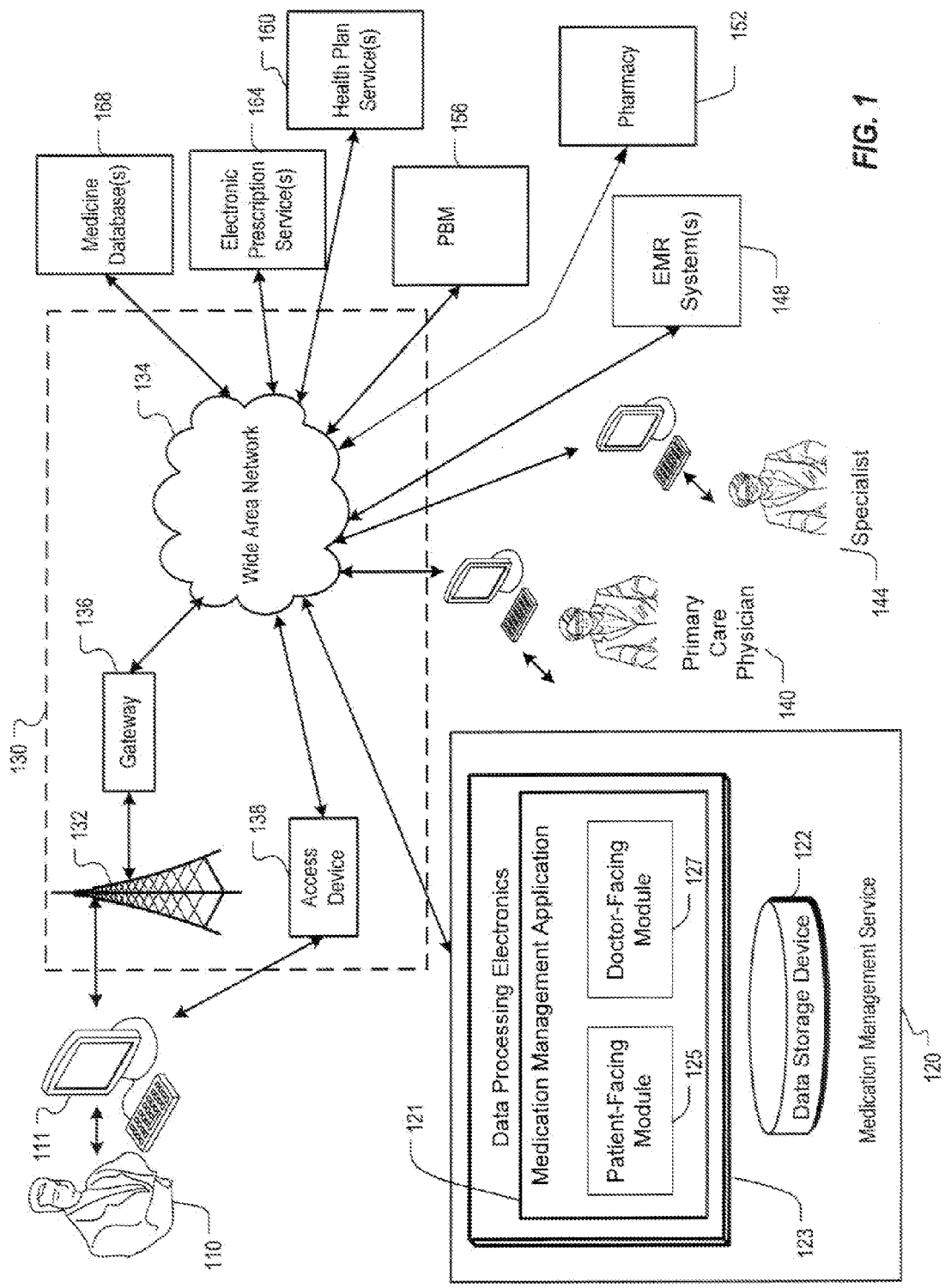
FIG. 1 illustrates an example network operating environment whereby patient medication data can be managed.

FIG. 1 illustrates an example network operating environment whereby patient medication data can be managed. A patient 110 can access a medication management service 120 over a communication network 130 to manage the patient's medication data. The patient 110 can use a data processing apparatus 111 to access the medication management service 120. The data processing apparatus device 111 can include one or more input devices (e.g. a mouse, a keyboard, etc.), and one or more output devices (e.g. a display device, speakers, etc.). The data processing apparatus can be a computer, a tablet computer, a handheld computer, a personal digital assistant, a mobile telephone, a smart phone, a network base station, an email device, a laptop computer, or a combination of any two or more of these data processing devices or other data processing devices.

The network 130 and the device 111 can communicate via one or more wired and/or wireless links. The network can include, for example, a wireless network 132, e.g., a cellular network by which a data processing apparatus, such as data processing apparatus 111, can communicate with a wide area network (WAN) 134, such as the Internet, by use of gateway 136. An access device 138, such as an 802.11 g wireless access device, can provide communication access to the wide area network 134. In some implementations, both voice and data communications can be established over the wireless network 132 and the access device 138. For example, the data processing apparatus 111 can place and receive phone calls (e.g., using VoIP protocols), send and receive e-mail messages (e.g., using POP3 protocol), and retrieve electronic documents and/or streams, such as web pages, photographs, and videos, over the wireless network 132, gateway 136, and wide area network 134 (e.g., using TCP/IP or UDP protocols). In some implementations, the data processing apparatus 111 can be physically connected to the access device 138 using one or more cables and the access device 138 can be a personal computer.

In the illustrated example, the medication management service 120 includes processor electronics 123 communicatively connected to a data storage device 122. The data processing electronics 110 can also operate a medication management application 121. The medication management service 120 can communicate with multiple users and services over one or more networks such as network 130. For example, the medication management service 120 can communicate with the patient 110, a primary physician 140 for the patient 110, other physicians such as a specialist 144 for the patient 110, one or more electronic medical records ("EMR") systems that can store prescription data for the patient 110, one or more pharmacies such as pharmacy 152 where the patient 110 purchases medications, a pharmacy benefit management service ("PBM") 156, one or more health plan service(s) 160 that can provide payment data from health plan providers regarding payment of claims, and one or more electronic prescription services 164. The medication management service 120 can obtain medication data for the patient 110 from these multiple users and can store the obtained data on a data storage device 112. For example, the medication management service 120 can obtain prescription data from the EMR system(s) 148. An example EMR system can be maintained by a doctor's office and provide prescription data written by physicians such as physicians 140 and/or 144. The pharmacy 152 can provide data regarding prescriptions filled by the patient 110. The PBM can provide prescription claims data received for prescriptions filled by the patient. Claims data for patient 110 can also be provided by the health plan service 160 (e.g., a managed care organization). The electronic prescribing service 164 can provide prescription data and/or prescription ordering data for the patient 110 that is routed, for example, through an electronic prescription hub.

The patient 110 can have an account with the medication management service 120 for accessing the medication management application 121. The medication management application 121 can have a patient interfacing module 125 that provides a user-interface through which the patient 110 can interact with the medication management service 120. Through the user-interface, the patient 110 can authorize the medication management application 121 to obtain medication data from one or more of the multiple sources. In some implementations, a third-party application can collect and store data from multiple sources; the patient can authorized the medication management application 121 to obtain medication data from such a third-party service.

Another source for medication data is the patient 110. The patient can interact with the medication management application 121 to enter data regarding medications the patient 110 is taking. For example, the patient can enter prescriptions received from a medical professional such as primary care physician 140 or a specialist 144. The patient 110 can also enter data regarding non-prescription medications, such as over-the-counter drugs, vitamins, nutritionals, and herbal products that the patient is taking.

The medication management application 121 can have a doctor interfacing module 125 that provides a user-interface through which one or more doctors such as the primary care physician 140 or the specialist 144 can interact with the medication management service 120. The primary care physician 140 and/or the specialist 144 can have an account with the medical management service 120. The following description regarding the primary care physician's 140 interaction with the medication management application 121 is equally applicable to any of the patient's doctors such as specialist 144, or another prescribing doctor if different than the primary care physician 140 or the specialist 144.

The doctor interfacing module 125 can present requests to resolve problems identified in the patient's 110 medication list and/or requests for cost savings alternatives to the physician. The medication management application 121 can manage patient medication data for multiple patients and can provide medication information, such as identified problems and/or requests for multiple patients, to the doctor interfacing module for presentation to e.g., the primary care physician.

The primary care physician 140 can provide updated prescription data to the medication management application 121. For example, the primary care physician 140 can prescribe new medications through an electronic prescribing application, e.g. that is provided by electronic prescription service 164. The prescription can be directed through an electronic prescribing hub to the pharmacy 152. The medication management application 121 can obtain prescription order data from the electronic prescription hub. If the prescriber does not have an e-prescribing application, the prescription can be sent electronically, by fax, by voice (telephone), or by letter directly to the pharmacy (or may be carried to the pharmacy by a person). In some examples, the prescriber can electronically send or fax the prescription through the medication management application.

Once the medication management service 120 obtains medication data from multiple sources, the medication management service 120 can compile a list of medications for the patient for reconciliation. Because the medication is obtained from multiple sources, the medication data can include multiple listings or identical entries for medications prescribed to the patient 110. Identical entries for medications include entries for the exact same container (e.g., bottle) of prescribed medication. For example, the medication management service 120 can obtain from the pharmacy 152 prescription data for a bottle of drugs purchased by the patient 110. Medication data obtained by the medication management service 120 from the PBM 156 can include claims data for the same bottle of drugs. Medication data obtained from the health plan service 160 can include prescription data for claims paid by the patient's health plan for the same bottle of drugs. The medication management application 121 may have also received an entry from the pharmacy and/or an entry from the patient for the same bottle of drugs. In some examples, the medication management application 121 can consolidate the identical entries in the list of medications. In some examples, the medication management application 121 can prompt the patient 110 to confirm that the entries are for identical medication.

In some examples, the duplicate entries represent a conflict that the needs to be resolved. For example, if the patient is unknowingly taking duplicate medications and believes that they are two different medications, this can be a potentially dangerous problem that needs to be resolved. On the other hand, it is possible that the patient is actually supposed to be taking both medications. For example, a patient may be taking a 5 mg tablet and a 2 mg tablet of the same medication for a 7 mg dose. Or, the patient may be taking the 5 mg dose on Mondays, Wednesdays and Fridays and the 2 mg dose on Tuesdays and Thursdays. Because the medication data, in some examples, may not include the instructions for taking the medication, the medication management application can confirm whether the patient is taking both medications. If so, the patient can provide a reason. If the reason is insufficient, the medication management application 121 can raise a conflict that needs to be resolved, e.g. with the help of a health care professional.

In some implementations, identifying identical medications can include matching all of the following criteria: a prescription number, fill date, drug name (either brand name or generic name or label name), drug strength, route of administration, quantity supplied, prescriber (e.g., Drug Enforcement Administration (DEA) number or National Provider Identifier (NPI) number), pharmacy (e.g., NPI number or National Association of Boards of Pharmacy number (NABP)). In some examples, the data received from the multiple sources may not contain sufficient information to identify affirmatively whether medications from two or more entries are identical. The medication management application 121 can confirm with the patient whether such data from the multiple sources includes data for identical medications. To assist in reconciliation, the system can identify for the patient the source of the data for the potentially identical medications. The medication management application 121 can present the consolidated list of medications, to the patient 110 in a user-interface. The patient 110 can provide the medication management application 121 an indication of medications on the patient list that the patient is no longer taking. The medication management application 121 can remove the medications the patient is no longer taking from the patient list displayed to the patient. In some examples, the medication management application 121 can verify with the patient the reason the patient is no longer taking the listed medication. For example, the patient may have discontinued the medication at a physician's direction, the patient 110 may have received a change in a prescription, etc. If the patient does not supply a reason why the patient is not taking a particular medication, e.g. the patient does not know why he/she is not taking a listed medication for an active prescription, then the patient can be prompted to contact the patient's physician i.e. the physician who prescribed the medication in question, if appropriate, based upon the medication. The medication management application 121 can also receive direction from the patient 110 to contact the primary care physician 140 or prescribing physician to verify whether the patient 110 should be taking the prescription.

The medication management application 121 can also identify duplicate medications in the medication data obtained from multiple sources. Duplicate medications are the same generic medications, same dose, same form, and same route of administration but have a different fill location or date. For example, a patient can have an existing prescription for a first drug under the first drug's brand name (e.g. Lasix 40 mg). The patient is admitted into the hospital and later discharged within the prescription period of the first drug. When the patient is discharged, the patient is given a second prescription for the same drug, same dose, and same route of administration but under a non-proprietary name (furosemide 40 mg). Both prescriptions remain active. The medication management application 121 can obtain data for both prescriptions.

In another example, a patient can be prescribed the same medication by two different doctors, such as a primary care physician 140 and a specialist 144 for the same or different conditions. Both prescriptions remain active. The medication management service 120 can obtain data for both prescriptions.

In some implementations, identifying duplicates for a first and second medication can include determining that all of the following criteria are met for the first and second medication: (1) an exact match of the following: drug name (either brand name or generic name or label name), drug strength, route of administration, and (2) coverage for the first medication overlaps with drug coverage for the second medication. Drug coverage can be calculated based on the file date of the drug and the day supply of drug filled on that date.

The medication management application 121 can prompt the patient 110 to confirm whether the patient is taking both medications. If the patient 110 supplies a reason why the patient 110 is not taking both, e.g. the patient understands the second prescription was meant to replace the first, then the prescription that the patient is not using can be eliminated from the patient list. If the patient indicates that the patient is taking medication from both prescriptions, the medication management application 121 can provide an indication to the patient to contact the prescribing physician regarding the duplicate medications. In some examples, the indication can include a link for the patient 110 to have the medication management application 121 contact the primary care physician 140 or prescribing physician.

The medication management application 121 can also identify similar medications in the medication data obtained from multiple sources. Similar medications are the same generic medication but one or more of the dose, form, and route of administration are different. For example, a patient can have an active prescription for medication administered orally and can have an active prescription for the same medication administered by injection.

The medication management application 121 can prompt the patient 110 to confirm whether the patient 110 is taking both medications. If the patient 110 supplies a sufficient reason why the patient 110 is not taking both, e.g. the patient understands the second prescription was meant to replace the first, then the prescription that the patient is not using can be eliminated from the list. If the patient indicates that the patient is taking medication from both prescriptions, the medication management application 121 can provide an indication to the patient to contact a physician regarding the similar medications. In some examples, the patient 110 can provide user input directing the medication management application 121 to contact primary care physician 140 (or the prescribing physician).

The medication management application 121 can also identify drug conflicts in the medication data. Drug conflicts include for example incompatible medications on the list (e.g. "drug-to-drug" interactions), drug-genomic conflicts (e.g. conflicts between a drug a patient's genetic make-up), drug-physiology conflicts (e.g. conflicts between a drug and a patient's physiology), drug-disease conflicts, drug-lab conflicts, drug-age conflicts, drug-allergy conflicts, etc. The medication management application 121 can obtain from a medicine database 168 a databank of information regarding drug-drug, drug-allergy, drug-disease, drug-age, and drug-lab interactions and the like. The drugs in the patient list can be compared against the drugs in the databank to determine any potential conflicts.

The medication management application 121 can present drug conflicts with the medication list to the patient 110 and indicate that the patient 110 should contact the patient's physician. The medication management application 121 can also present information regarding the risks involved with the conflict to the patient 110. In some examples, the patient 110 can provide user input directing the medication management application 121 to contact the primary care physician 140 or prescribing physician regarding the conflict.

The medication management application 121 can provide information regarding problems on the patient's medication list, such as duplicate medications, similar medications, poor adherence, failure to purchase prescribed medications, and drug conflicts, to the primary care physician 140 via a secure user-interface on the doctor interfacing module 127. For example, when the medication management application 121 identifies a problem on the patient's medication list, the account for the primary care physician 140 or prescribing physician can be updated with the problem. The medication management application 121 can send a notification to the primary care or prescribing physician to access his/her account on the medication management application 121 to address the problems. The notification can be sent via email, pager, text message, phone call, fax, or the like. In the notification sent to the primary care physician, the severity of the problem can be indicated so the primary care physician can assess the urgency with which to access his/her account with the medication management application 121.

When the primary care physician 140 logs onto the medication management application 121, the physician can address the problem using the medication management application 121. For example, the primary care physician 140 can indicate that no change should be made to medications involved in the problem. In such a case, the medication management application 121 can provide an indication to the patient 110 that the problem has been resolved and no change is to be made.

The primary care physician 140 can indicate that one or more medications involved in the problem should be discontinued. The medication management application 121 can update the patient medication list on the patient's account by removing the discontinued medications. The medication management application 121 can also notify the patient 110 of the discontinued medications and can receive confirmation from the patient 110 that the patient is no longer taking the discontinued medications.

The primary care physician can indicate that a new medication should be prescribed. In some examples, the primary care physician 140 can electronically prescribe a new medication through the medication management application 121. In some examples, the medication management application 121 can provide the primary care physician 140 with a link to the electronic prescription system 164 to write a new prescription. The patient 110 can be notified of the new prescription. The new prescription can appear in the patient list and become an active entry as soon as prescription order data, prescription fill data, prescription claims data, etc., is received by the medication management application. If the new prescription replaces a medication on the patient list, an indication can appear on the patient list that a new medication has been prescribed. When medication data, e.g. claims data from the PBM 156, indicates that the prescription has been filled, the medication reconciliation process takes place, and the new information from the patient and prescriber incorporated. Confirmation of the patient's understanding of what they should be taking can result in the replaced medication being removed from the patient list and the new medication being added to the patient list. The medication management application 121 can also notify the patient 110 of the discontinued medications and can receive confirmation from the patient 110 that the patient 110 is no longer taking the discontinued medications.

The medication management service 120 can also identify cost savings based on medications listed in the patient list and the benefit structure of the patient's plan. Cost savings can include therapeutic switches to less expensive generic alternatives, generic switches, tablet splitting, alternate suppliers (e.g., different pharmacies, mail order vs. retail, etc.), and long-term supply.

A therapeutic switch includes replacement of medication with a chemically different medication within the same therapeutic category, e.g., generic simvastatin for brand name Lipitor. A generic switch includes substituting a medication with a lower-priced medication having the same generic chemical entity in the same dosage marketed by a different company, e.g., generic simvastatin for brand name Zocor. For tablet splitting, the medication management application 121 can identify medications that cost less per gram when purchased in larger tablets and split manually (e.g. splitting a 80 mg tablet into two 40 mg halves instead of two 40 mg tablets); the medication management application 121 can identify medications that are manufactured in a form which allows tablet splitting, and do not have a narrow therapeutic index. The medication management application 121 can identify medications on the patient list that cost less when purchased in a long term supply (e.g. 90 day supply vs. a 30 day supply). The medication management application 121 can identify medications on the patient list that cost less when purchased at an alternate location, for example a different retail pharmacy or a mail-order pharmacy.

Cost savings to the patient can depend on the medical plan of the patient 110. The medication management application 121 can obtain from the PBM 156 cost savings to the patient for medications on the patient list based on the patient's medical plan. In some examples, cost savings include cost savings for the patient 110 such as at the point of purchase at the pharmacy 152. For example, the patient may have a tiered benefit plan, where the patient pays a higher co-pay for a brand name drug than for the generic alternative. In some examples, cost savings can include cost savings to the health plan for the patient. For example, the patient may have an identical co-pay for a therapeutic switch whereas the health plan pays a lower price for the therapeutic switch.

The medication management application 121 can generate a list of one or more potential cost savings and present this list to the patient 110. The patient can select from the listed cost savings. When the patient selects an identified cost savings that requires physician's intervention, such as therapeutic switches, the medication management application 121 can direct the requested cost savings to a physician, e.g. the primary care or prescribing physician's account in the medication management application 121. The doctor can be notified of the request. When the primary care physician 140 accesses the medication management application 121, the request appears in a secure user-interface where the primary care physician 140 can issue a new prescription. The new prescription can be sent to the pharmacy 152 and can appear in the patient list for the patient 110 when the patient accesses the medication management application via the data processing apparatus 111. When the medication management application 121 obtains medication data that indicates the prescription is filled, the medication management application 121 can update the patient list in the patient interfacing module 125. The medication management application 121 can verify with the patient 110 that the patient has discontinued any medications that the prescription has replaced.

The medication management application 121 can constantly obtain medication data for the patient 110 from multiple sources to keep the patient list up-to-date. For example, the medication management application 121 can monitor the prescription data and claims data from multiple sources. The medication management application 121 can also maintain data regarding medications that were removed from the patient list (e.g. a complete listing of drugs), medications that were prescribed but never filled, and medications that were considered for the patient list and the reason they were not added. As new medication information is obtained for the patient 110, the medication management application 121 can compare this new medication information against the complete list of drugs maintained for the patient to identify identical medications, so that identical entries are not later added to the patient list that were already removed or considered.

In some examples, if prescription data includes a discontinuation date for a particular prescription, the medication management application 121 can remove a listing for that prescription from the list presented to the patient (e.g. the active list). In addition, medications, e.g. non-maintenance medications, without a discontinuation date can be removed from the medication list presented to the patient if the fill date plus the number of days in the supply has passed and no additional fills are noted within a predetermined time period.

If the number of days in the supply of a filled prescription has passed and the medication data indicates the prescription has been refilled, the patient's medication list can be updated with the refilled prescription. If the number of days in the supply has not passed and the medication data from one or more sources indicates that the patient has refilled the prescription, the medication management application can identify the overlap to the patient and confirm with the patient that the patient is not taking both medications at the same time.

In some examples, the medication management application 121 can identify medications that were prescribed but never filled from the medication data from multiple sources. For example the medication management application 121 can receive prescription data from the electronic prescription service 164 indicating a new medication has been prescribed. If other medication data, such as claims data from the PBM and/or the health plan service 160, indicates that the prescription was never filled, the medication management application 121 can notify the patient of the unfilled prescription. The medication management application 121 can also notify the patient's primary care physician 140 or other prescribing physician of the failure to fill the prescription, for example, upon direction of the patient.

The medication management application 121 can also receive from the patient 110 a reason why the patient 110 did not fill the prescription. The reason can be provided to the patient's primary care physician 140 or other prescribing physician. The patient's primary care physician 140 or other prescribing physician can provide a resolution such as changing the patient's prescription, replacing the patient's prescription, discontinuing the prescription, and/or providing feedback to the patient etc.

In some examples, the medication management application 121 can determine the out-of-pocket cost to the patient 110 for the unfilled prescription. If the cost exceeds a predetermined amount, the medication management application 121 can determine less-expensive alternatives and/or can notify the patient's primary care physician 140 or other prescribing physician. If alternatives are available, the alternatives can be presented to the patient. Upon receiving input from the patient requesting the alternative, the medication management application 121 can provide the request to the patient's primary physician 140, other prescribing physician, and/or pharmacy for approval. Upon approval, the patient's medication list can be updated.

FIG. 2 shows an example user-interface 200 for helping a patient reconcile a medication list 210. Before the user-interface 200 is presented to the patient, medication data for prescription medications that the patient is taking can be obtained from multiple sources, such as by a medication management application. Identical listings can be consolidated and an interactive patient medication list 210 can be presented in the user-interface 200. The user-interface 200 has a listing of the patient's name at 213, a medication allergies list 216 for medications the patient is allergic to, which in this example includes penicillin. The user-interface 200 includes a button 218 for inputting new allergies and an option to print the list 221. In the illustrated example, the patient medication list 210 includes a listing of multiple medications for the patient with a first column 223 for listing a drug name for each of the listed medications and a second column 226 for listing a prescriber for each listed medication, and a third column 229 for receiving user input from the patient to indicate whether the patient is no longer taking the listed medication. For example, if the user selects a box 230 in the third column 229 for the medication carbamazepine, the system will remove carbamazepine from the list. The user-interface 200 also includes a new-medication button 233 for entering new medications.

Example entries in the patient medication list 210 include a first entry 250 for Lasix 40 mg, a second entry 251 for furosemide 40 mg, a third entry 252 for ibuprofen 600 mg, a fourth entry 253 for Plavix 75 mg and fifth entry 254 for Nexium 4 mg. The prescriber for the medication in the first entry 250, Dr. Jones, is listed in the second column. The prescriber for the medication in the second entry 251 is unknown from the obtained medical data and is listed accordingly in the second column. The prescriber for the medication in the third entry 252, Dr. Adams, is listed in the second column. In some examples, the source of the entry can be displayed with the medication list or upon receiving user input to help the patient identify where the data for the entry came from.

Figure 3A:
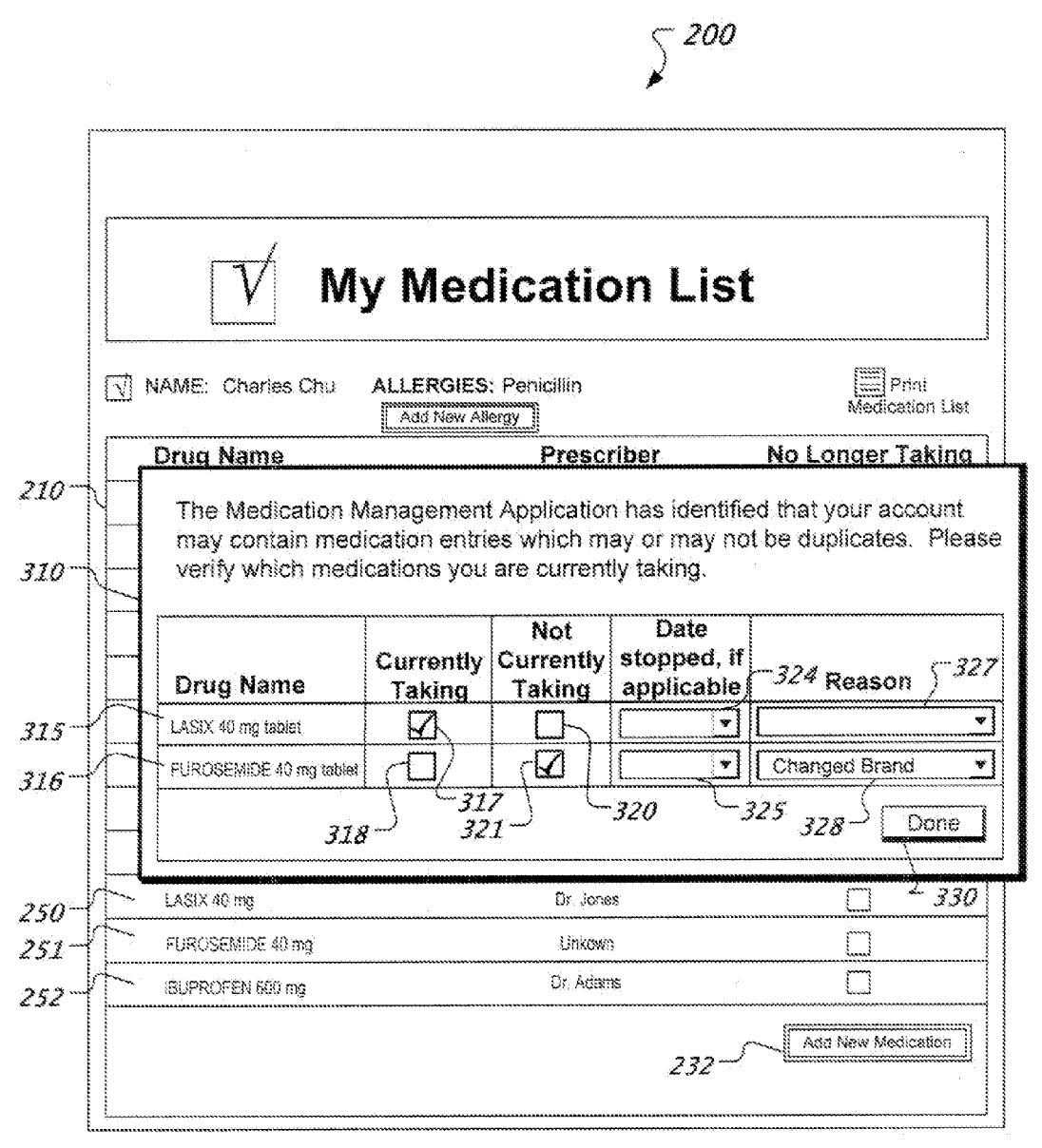

FIG. 3a shows the user-interface 200 with an example pop-up window 310 for reconciling duplicate medications. A similar pop-up window can be used for reconciling similar medications. Duplicate medications on the user list can be determined by a medication management application and then presented to the patient for reconciliation. The window 310 includes a listing of two duplicate medications, a first medication 315 (LASIX 40 mg tablet) and a second medication 316 (furosemide 40 mg tablet). The patient can indicate in selectable boxes 317 and 318 whether the patient is taking the first and second listed duplicate medications respectively. And, the patient can indicate in selectable boxes 320 and 321 whether the patient is not taking the first medication 315 and the second medication 316 respectively. In fields 324 and 325, the patient can indicate a date when the patient stopped taking the respective medications, if applicable. In fields 327 and 328, the patient can indicate a reason the medication was stopped. The pop-up window can also include a "done" button 330 for indicating that the user has finished inputting data, and the patient mediation list 210 can be updated according to data input into window 310.

In the example shown in FIG. 3a, the patient has selected box 317, indicating that the patient is currently taking the first medication 315 and has selected box 325, indicating that the patient is not currently taking the second medication 316. When the user selects the "done" button 330, the patient medication list 210 is updated to remove the second medication 315. FIG. 3b shows the patient medication list 210 with the example entry 251 for furosemide removed.

Figure 3C:
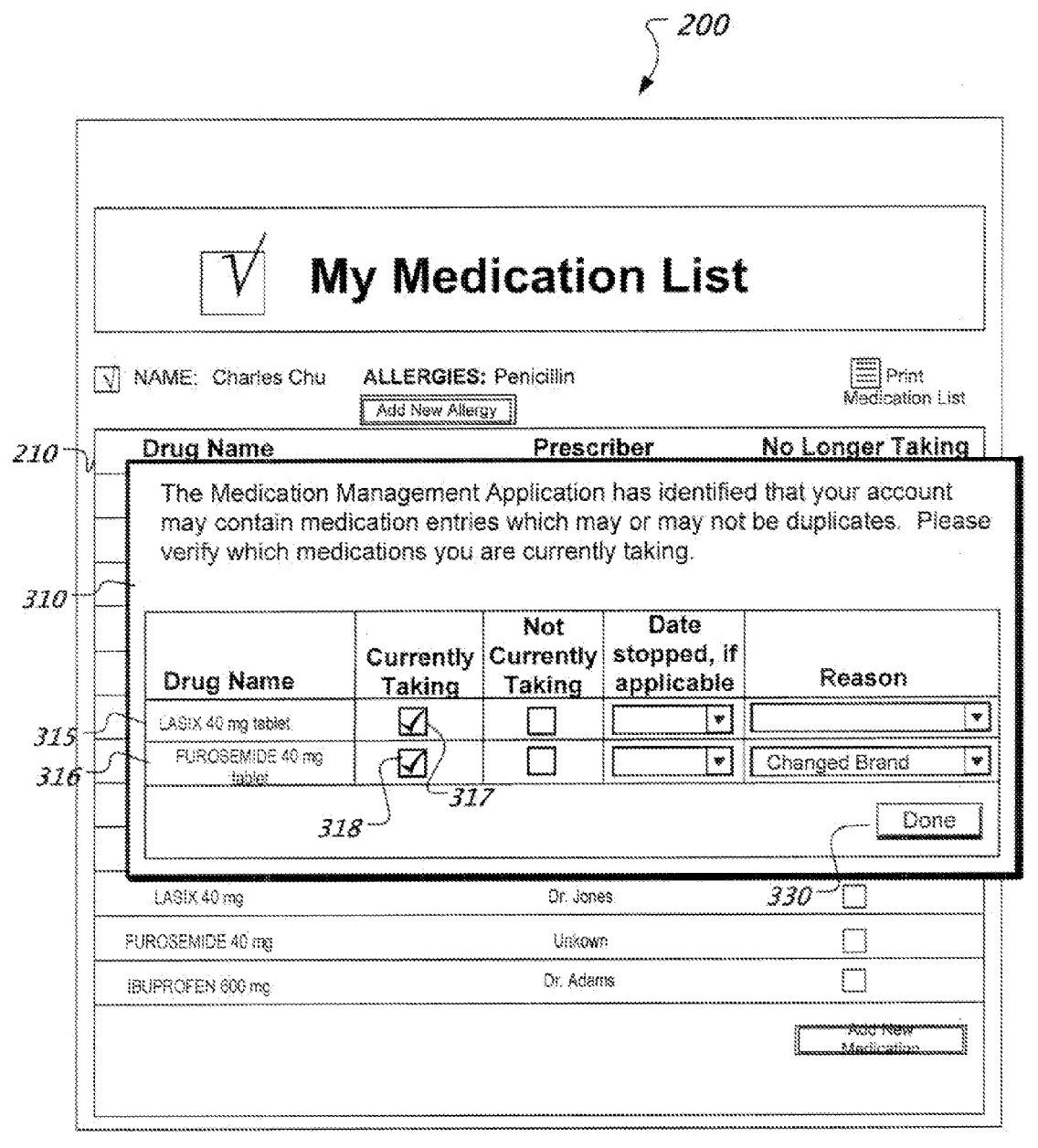
Figure 3D:
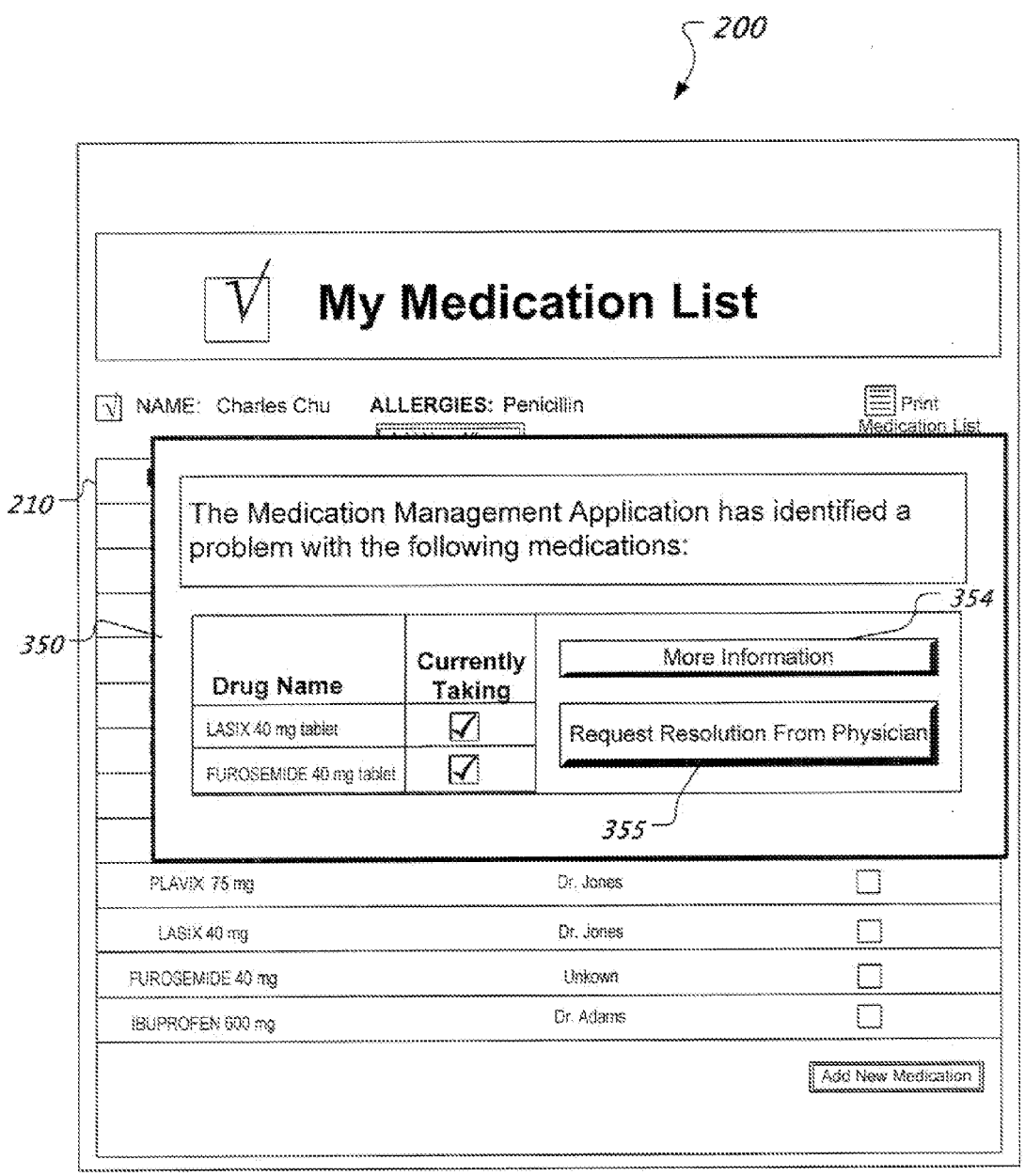

FIG. 3c shows the user-interface 200 with the boxes the box 317 selected and box 318 selected, indicating that the patient is taking both the first medication 315 and the second medication medications 316. When the patient selects the "done" button 330, another pop-up window 350 is presented as shown in FIG. 3d with information regarding a potential problem, i.e. taking duplicate medications (or similar medications). The pop-up window 350, indicates that the patient may be taking medications, i.e. Lasix and furosemide, that may be unnecessary duplicates. The pop-up window 350 includes a "more information" button 354 for obtaining more information regarding the problem. The pop-up window 350 includes notification button 355 for notifying the patient's health care professional (e.g. primary care physician or prescribing physician) regarding the potential problem. Upon selection of the notification button 355 the medication management application notifies the patient's health care professional of the potential problem. Meanwhile the patient medication list 210 can include an indication with the first entry 250 and the second entry 251 that they are currently pending resolution by the patient's physician.

In some examples, the medication management application can be preset to automatically direct identified problems to a third-party for resolution, such as a care-taker and/or or a health care professional. In some examples, another user, such as a caretaker, can be authorized to log-in to the patient's account to help reconcile the patient's medication list and request resolution to problems in the list.

The patient's health care professional can access the medication management application to view a list of potential problems on the patient's medication list. Using the medication management application, the patient's health care professional can discontinue one or more of the patient's listed medications, add a new prescription, and/or replace a prescription with a new prescription. For example, if the patient's health care professional determines that the patient should not be taking both the first medication 315 and the second medication 316, the health care professional can discontinue one of the medications, such as the Lasix 40 mg prescription. FIG. 3e shows the patient medication list 210 updated according to health care professional's change with the first entry 250 for Lasix 40 mg prescription removed. FIG. 3e also shows a listing 360 that the prescription was discontinued by the physician and that the patient should stop taking the discontinued medication. The listing 360 includes a selectable physician's notes button 362. Upon selection of the physician's notes button 362, notes from the physician can be displayed explaining why the medication was removed. The listing 360 also includes a confirmation button 364 where the patient can confirm that the patient has discontinued the removed medication.

FIG. 4a shows user-interface 200 with a pop-up window 410 for indicating conflicts in the medication list 210. A first entry 415 for a first medication, Nexium, from the patient list 210 (see entry 254 on patient medication list 210) is identified as conflicting with a second medication in a second entry 416, Plavix, from the patient list 210 (see entry 253 on patient medication list 210). The patient can select a "more information" button 420 to learn more about the conflict. The patient can also select a notification button 455 for notifying the physician of the conflict and to request resolution. The entry 253 on the medication list 210 for Plavix and the entry 254 for Nexium on the medication list 210 can have an indicator that they are pending resolution from the physician.

When a resolution is received from the physician, the patient medication list 210 can be updated accordingly. For example, in FIG. 4b a listing 460 is displayed indicating the prescription for Plavix was discontinued by the physician and that the patient should stop taking the discontinued medication. The entry 253 for Plavix was removed from the patient list 210. The listing 460 includes a selectable physician's notes button 462. Upon selection of the physician's notes button 462, notes from the physician can be displayed explaining why the medication was removed. The listing 460 also includes a confirmation button 464 where the patient can confirm that the patient has discontinued the removed medication.

Figure 5A:
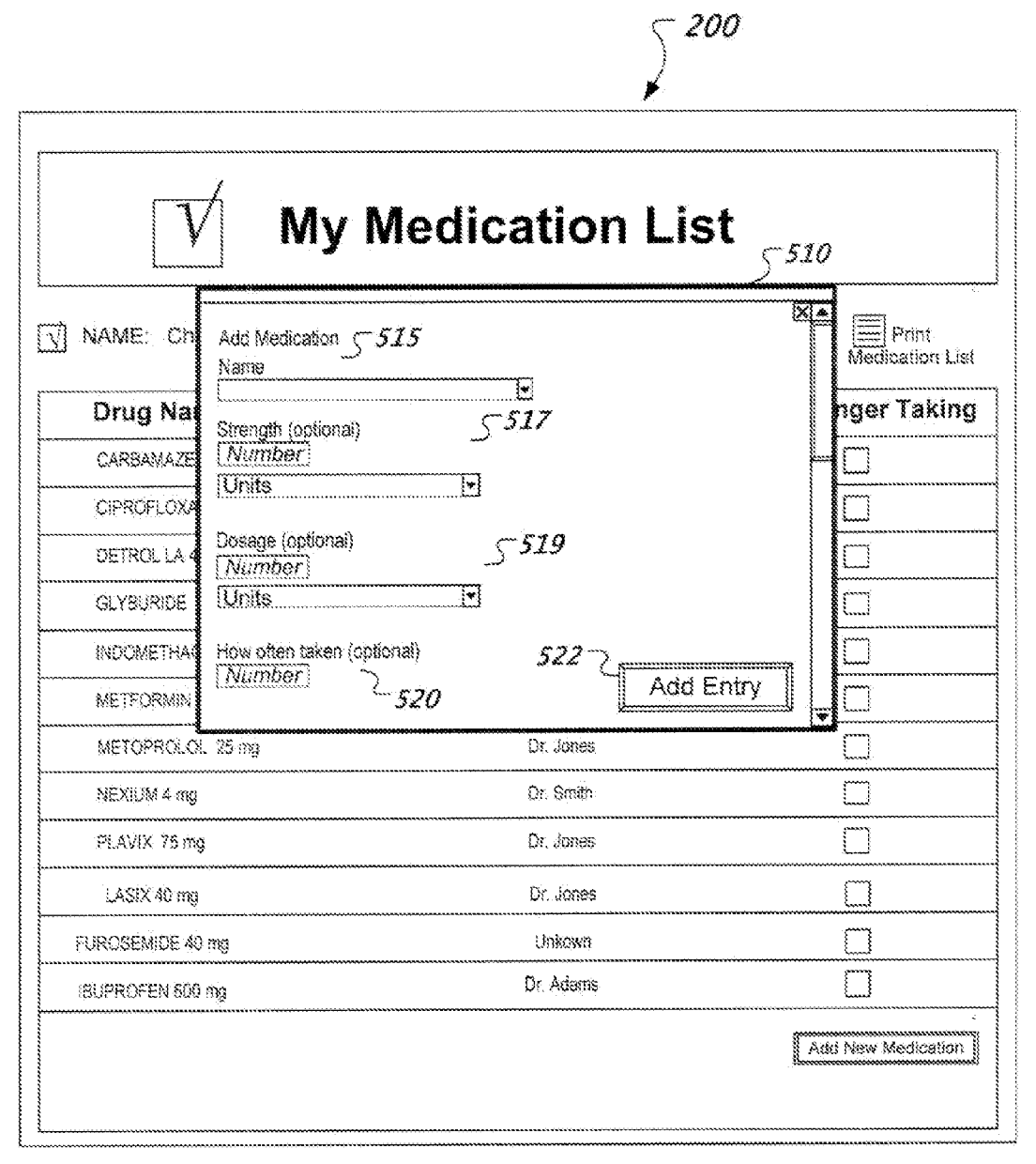

FIG. 5a shows the user-interface 200 with an example window 510 for entering new medications manually. For example, when the patient selects the new-medication button 233, the window 510 can be presented for entering a new medication. The window 510 includes a name entry field 515 for entering the name of the drug, strength fields 517 for entering strength of each pill, optional dosage fields 519 for entering the dosage amount, frequency field 520 to enter how often the medication is taken, and a button 522 for adding the medication to the patient list 210.

Figure 5B:
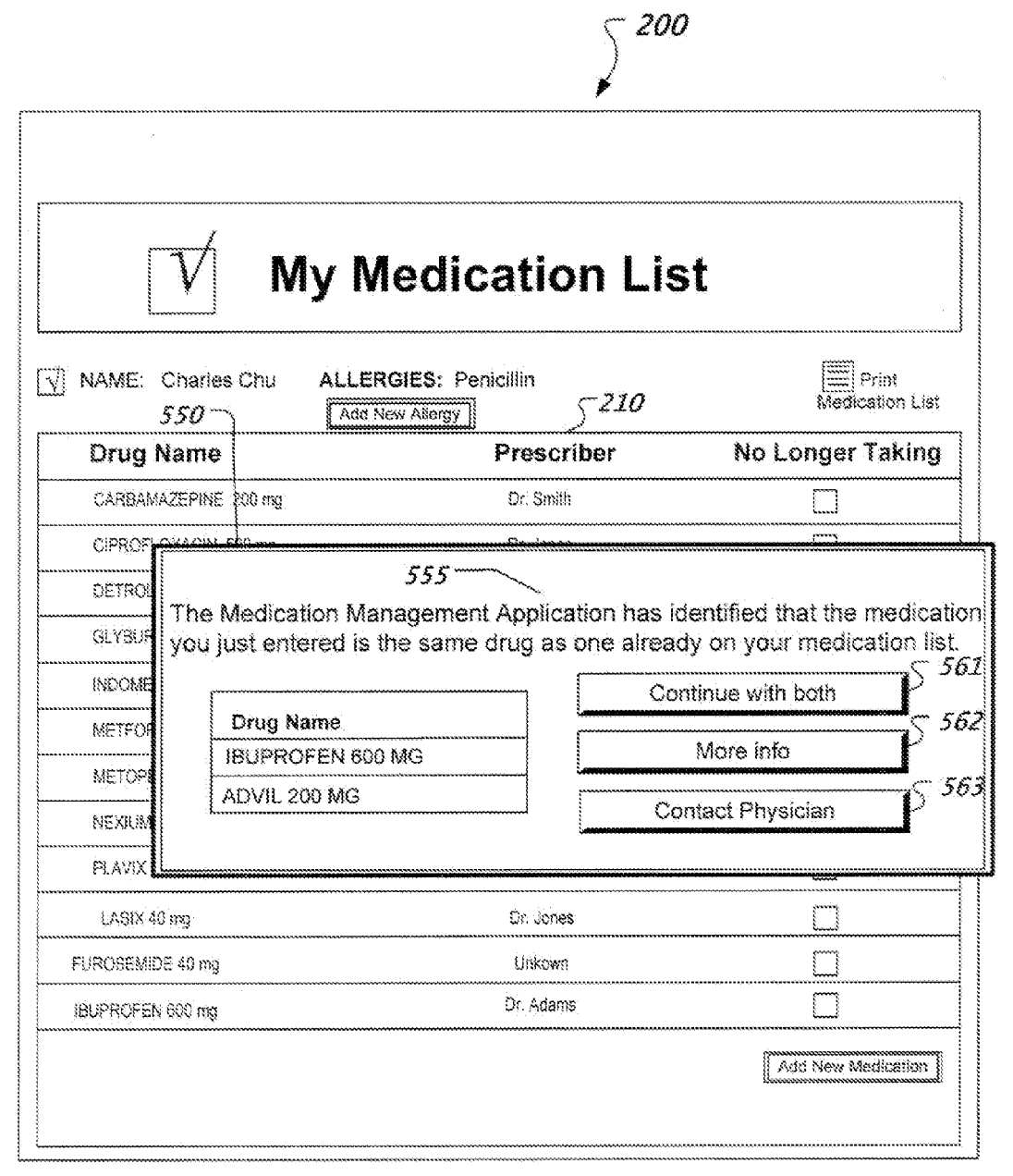

FIG. 5b shows a window 550 for indicating a problem with a newly added medication by the patient. The newly added drug in this example is a non-prescription medication—Advil at 200 mg. The window 550 includes an explanation 555 of the problem—that the medication entered is the same drug as one already on the patient medication list 210. The window presents the patient with a selectable option 561 to continue with both medications, with a selectable option 562 for more information regarding the listed problem, and a selectable option 563 to contact the patient's physician regarding the problem for help resolving the problem. The physician can indicate whether it is safe to take both medications, and/or can recommend an alternative over-the-counter or prescription medication, can indicate one of the medications should be discontinued, and/or can give additional or alternative recommendations. The patient medication list 210 can be updated accordingly.

FIG. 6a shows the user-interface 200 with an example window 610 for presenting potential cost savings. Cost savings can be identified for the medications on the patient list 210, e.g. by the medication management application. A selectable cost savings icon 615 is shown next to an example entry 616 for a drug named Lipitor. The icon 615 indicates that there is a potential cost savings with the listed medication. The patient can select the icon 615 to display the window 610. The window 610 includes an indication of the potential cost savings if switched to a similar therapeutic alternative. The window 610 also includes a selectable button 621 for sending a notification to the patient's physician requesting the similar medication. The patient can also select a button 622 to obtain more information about the cost savings alternative. Example cost savings that can be identified and requested in this manner can include therapeutic switches, generic switches, tablet splitting, long-term supply etc. For cost savings that require only the pharmacy's intervention, e.g. requesting a long-term supply, the request can be sent directly to the pharmacy.

The patient's physician can be notified via one or more notification methods, including fax, handheld device, email, phone etc. of the requested change. Also, when the patient selects the button 621, the request can be loaded into an account for the patient's physician e.g., in the doctor interfacing module on the medication management application. The patient's physician can access his/her account with the medication management application to review the request and to grant or deny the request. If the request is denied, the patient is notified accordingly and can be provided an explanation. The patient medication list 210 can be updated accordingly by removing the icon 615. If the request is granted, the physician can issue a new prescription e.g. in the medication management application, via an electronic prescription service, etc.

When the new prescription is issued, the prescription data can be obtained by the medication management application and presented to the patient with the patient list 210 in the user-interface 200 as shown in FIG. 6b. The prescription data is shown in window 670 below the patient list 210, indicating that a replacement prescription for Lipitor is available at a particular pharmacy. The replacement prescription, in this example, is simvastatin 10 mg which can be an alternative to Lipitor. The window 670 also shows potential cost savings for the patient using this replacement.

FIG. 6c shows an updated patient medication list 210 that is updated with the prescription is filled. Medication data can be obtained e.g., from the pharmacy, from a PBM etc. that indicates that the patient filled the prescription (i.e. purchased the newly prescribed medication). The patient medication list 210 is updated with the added prescription at entry 668, an entry for simvastatin 10 mg. Also, the list 210 can include an indication of the medications removed at entry 660. The entry 660 can include a button 665 for viewing physician's notes about the switch and can include a button 666 for the patient to confirm that the patient has discontinued the medication listed in entry 660.

In some implementations, the medication management service 120 can include an incentive mechanism to award a patient for updating the medication list. A patient can receive points for using the user-interface 200 to maintain an updated medication list. Points can accumulate as the patient resolves problems and/or has problems resolved on the list. Points can also accumulate as the patient requests cost savings changes to their medication list. Points can also accumulate as the patient improves and/or maintains good adherence to their medications. The points can be redeemed by the patient for rewards such as for savings on co-payments and/or for other prizes.

FIG. 7 shows an example user-interface 700 for displaying an interactive patient medication list 710 in the form of a personal health report card 720 for a patient. The personal health report card 720 includes medication data for current and past prescriptions for the patient. The drugs in the patient medication list 710 are organized into a first group 711 for maintenance medications and a second group 712 for non-maintenance medications. Each of the groups is sub-categorized into patient-friendly drug groupings. For example, under the first group 711, there is a first category 721 with medications that fall under a "Nervous System (Brain and Pain)" drug grouping and a second drug grouping 722 with medications that fall under a "Heart and Lung" category. Within these drug groupings, the drugs are further sub-categorized into medication sub-groupings. These medication sub-groupings are used for adherence calculations, in order to take switches into account. The non-maintenance medications are also sub-categorized.

Under each group, the medications are listed in a first column 731 by the drug name and strength. A second column 732 shows the dispensed dates and duration of dispensed medications in a timeline. The timeline for each medication has an indicator, e.g. indicator 788, for refill date, and shows the duration 789 of each prescription filled and gaps between duration and next refill. The duration can be based on an ongoing summation of drugs from each of the refills in that prescription. A third column 733 shows an adherence rating 791 for each medication or medication grouping. An adherence rating indicates how compliant the patient has been in obtained a filled prescription or prescriptions over time. The adherence rating 791 shown for the medications listed is based upon a medication grouping, so that dose changes or therapeutic switches are taken into account. For example, an entry 792 for clozapine and another entry 793 for Geodon are both grouped under the first category 721 for Brain and Pain and are also sub-categorized together into a medication grouping so that they have a common adherence rating 794.

In the example shown, entry 792 for clozapine and the entry 793 for Geodon are both antipsychotic medications and therefore are sub-grouped together into a predetermined antipsychotic medication grouping. Medication data received regarding refill date and duration for these two medications indicates that clozapine was being taken from January 2011 through April of 2011 and that a switch was made to Geodon which was being taken from May 2011 through June 2011. Because the adherence rating is based on the adherence to both clozapine and Geodon, the adherence rating 794 shows four stars for this time period.

Problems in the medication list can be identified and listed under the problems heading 740. For example, a polypharmacy problem can be identified based on the number of different prescriptions, prescribers, and pharmacies for the medications in the list. Polypharmacy problems are listed under the polypharmacy sub-heading 742. A risk rating for the polypharmacy problem can be indicated by the number of risk signs 743. In some examples, the patient can provide user input in the user interface 700 to have a physician, physicians, pharmacy and/or pharmacies contacted regarding the identified polypharmacy problem. For example, the risk signs 743 can be user-selectable to provide the patient with options regarding who should be contacted regarding the identified polypharmacy problem. In some examples, the patient can be advised to obtain his or her prescriptions from a single pharmacy to reduce the polypharmacy risk.

Also, duplicates, similar medications, prescriptions never filled, and conflicts can also be listed under the problems heading 740. For example, a sub-heading 744, titled medication alerts indicates problems with therapeutic duplication for two of the drugs on the patient medication list with active prescriptions—morphine and hydrocodone. A risk level for the therapeutic duplication can be indicated with a number of risk signs 747. The patient is presented with the option to notify his/her physician of the therapeutic duplication by clicking button 748. The physician can review the therapeutic duplication and can resolve the problem. If the resolution includes a new prescription, the prescription can be sent to a pharmacy and the patient can be notified of the new prescription in the user interface 700.

Figure 8:
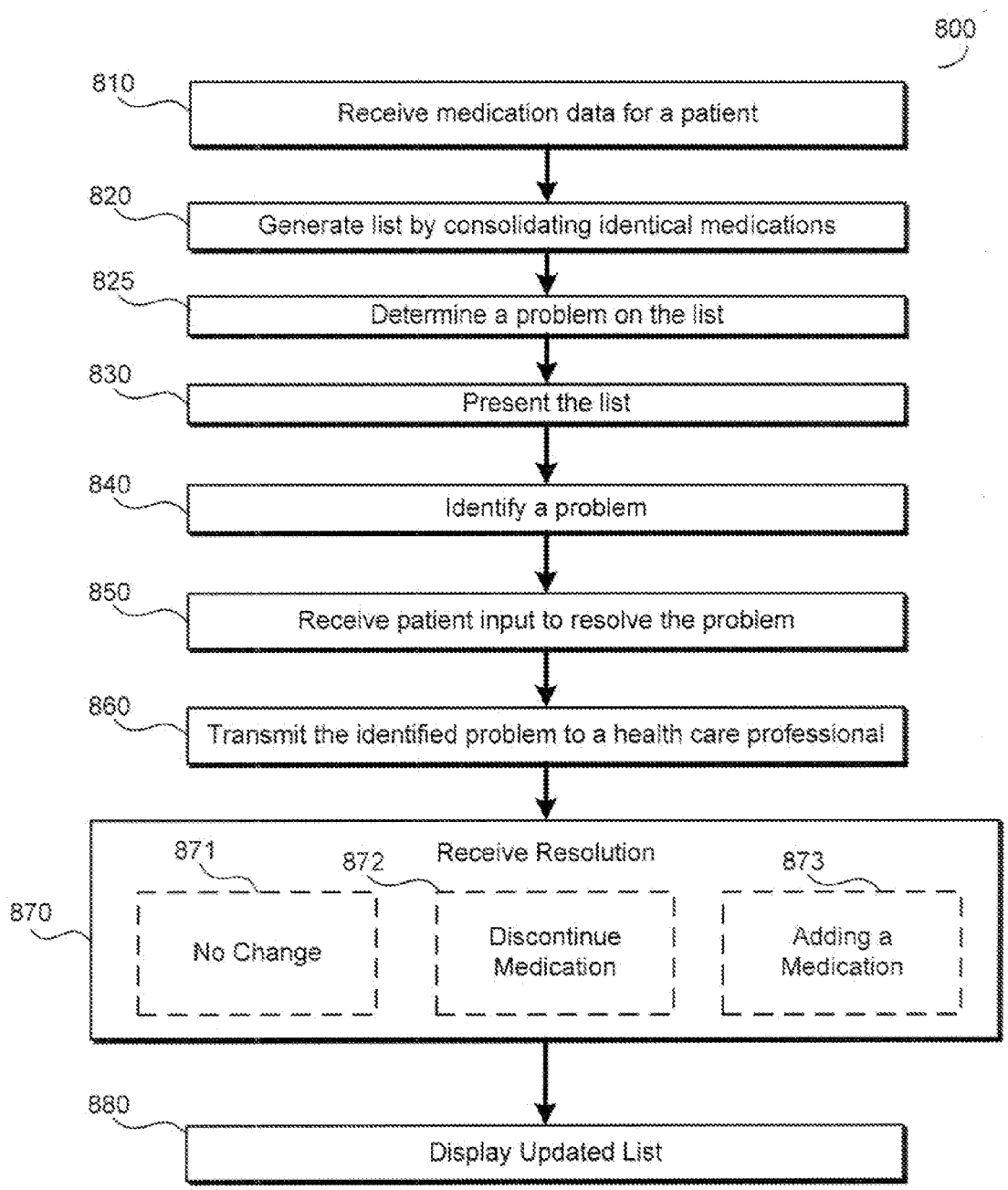
FIG. 8 shows an example process for updating a patient medication list.

FIG. 8 shows an example process 800 for updating a patient medication list. At 810, the process 800 receives medication data for a patient from multiple sources. Medication data can include prescription data such as: order data regarding a prescription written by a physician, fill data regarding a filled prescription, and claims data regarding claims for a filled prescription. Medication data can also include data regarding non-prescription or prescription drugs entered by the patient such as herbal, nutritionals, and supplements entered by the patient; also, medications obtained without records, such as physician office samples and low-cost generic medications furnished by certain pharmacies in which no claim is submitted, etc. The multiple sources can include, for example, one or more health care professionals, EMR systems, pharmacies, a PBM, health plan services, electronic prescribing hubs, the patient, etc.

At 820, the process generates a list of medications for the patient by consolidating identical medications. For example, the process can identify and consolidate identical medications in the medication data. At 825 one or more problems in the list of medications is determined. Problems on the drug list can include duplicate medications, similar medications, conflicts etc. At 830, the list of medications is presented to the patient in a user-interface. The list can be interactive so as to provide various functionalities to the patient. At 840, the process 800 identifies for the patient one or more of the problems in the medication list. For example, a problem can be identified with the presentation of the list itself and/or in a pop-up window. The problem can be identified in a manner so that the patient can resolve or request resolution to the problem. At 850, the process 800 can receive patient input to resolve the problem. For example, the patient can indicate that a health care professional such as the patient's physician should be contacted for resolution of the problem. At 860, the identified problem is transmitted to the health care professional for resolution. The details of the identified problem can be transmitted to a secure user-interface while a notification is sent to the health care professional directing the health care professional to access the secure user-interface to resolve the problem.

At 870, a resolution is received. The resolution can be received directly from the physician. In some examples, the resolution can be determined from medication data downloaded from one or more of the multiple sources, such as prescription data or claims data. The resolution can be an indication from the health care professional that no change 871 should be made to the prescribed medications involved in the identified problem. In some examples, a physician can determine the risks posed by an identified problem are outweighed by the benefits of adhering to prescriptions with medications involved in the problem. The medication list can be updated to include an indication that no change should be made. Also, the resolution can be to discontinue 872 one of the medications involved in the problem, such as one of multiple conflicting medications, one of multiple duplicate medications, one of multiple similar medications etc. In some examples, the resolution can be adding 873 a medication. For example, the health care professional can prescribe a new medication to replace one or more of the medications involved in the conflict. Multiple problems can be identified on the medication list and can be resolved as described above.

At 880, an updated medication list is displayed to the patient. The medication list is updated according to the resolution received. For example, if no change is made then the list can be updated to indicate the problem has been resolved and that the patient should continue taking medications on the list as prescribed. For discontinued medications, the process 800 can remove those medications from the medication list. Also, an indication can be displayed to the patient requesting confirmation that the patient has discontinued the removed medication. For new prescriptions, the medication list can be updated with an indication that a new prescription is available. When the prescription is filled, the newly prescribed medication is added to the list. If the prescription is replacing a medication already on the medication list, the process can remove the replaced medication. The process 800 can also receive a verification from the patient that the patient has discontinued the removed medication.

Figure 9:
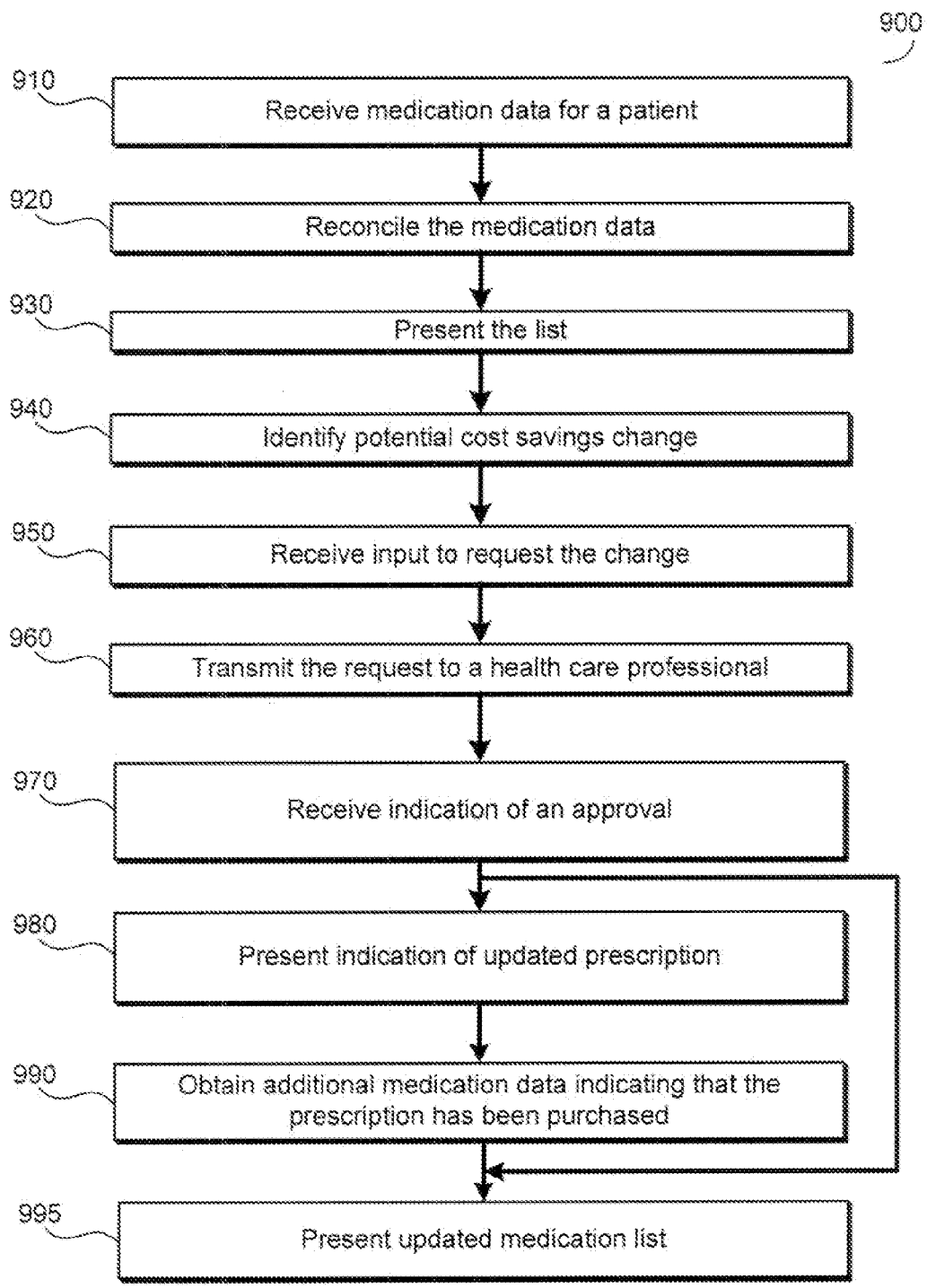
FIG. 9 shows an example process for updating a medication list.

FIG. 9 shows an example process 900 for updating a medication list. At 910 medication data is received for a patient from multiple sources. For example, the medication data can include entries for multiple medications in the form of prescription data, claims data for prescription medications, and/or patient entered data regarding medications the patient is taking. At 920, the process reconciles the medication data from the multiple sources to generate a reconciled list of medications for the patient. Reconciling the medication data from multiple sources can include identifying and consolidating entries for identical medications. Reconciling can also include identifying and resolving problems with medications in the patient list such as duplicate medications, and similar medications. In some examples, the process 900 can also optionally determine problems in the reconciled list and can receive user input to resolve those problems.

At 930, the reconciled list is presented to the patient in a user-interface. The reconciled list can be interactive to allow the patient to obtain information regarding the medications on the list. For example, the user can obtain information regarding the source of the information for the medications on the list. At 940, a potential cost savings change for a prescribed medication on the list is identified, for example on the list or in a pop-up window. The cost savings can be identified based on the patient's health care plan. The health care plan data can be obtained for example from a PBM. The cost savings can be savings for the patient or the health care plan provider. Cost savings can include therapeutic switches, generic switches, tablet splitting, long-term supply etc. The potential cost savings change can be identified for the patient on the patient list. The patient can also request additional information regarding the cost savings change.

At 950, input is received to request the cost savings change for the prescribed medication. In response to receiving the selection, a request for the cost savings is transmitted 960 via a network to a health care professional. For example, the request can be provided to a health care profession in a secure user-interface on a data processing apparatus. The health care professional can grant or deny the request. An indication of an approval for the request can be received at 970.

In some examples, a pharmacist can grant the request for certain cost savings changes. For example, depending on the prescription, the pharmacist can approve a switch to a generic alternative. In such a case, an approval for the switch can be received from the pharmacy.

In some examples, a new prescription can be required in order to grant the request. A health care professional such as a physician can grant the request by providing a new prescription. Data regarding the updated prescription can be received from the health care professional via the network and/or from another source that provides claims data and/or prescription data. At 980, an indication of the updated prescription is presented to the patient. The indication of the updated prescription can include information regarding the new medication and to which pharmacy the prescription was sent.

At 990, additional medication data can be obtained from one or more sources that indicates that the prescription data has been purchased. For example, the additional data can include for example claims data or prescription data that the prescription has been purchased. In some examples, data from multiple sources can be received identifying that the new prescription has been purchased. The data for medication from these multiple sources can be identified as identical medications and consolidated into one medication entry.

If no prescription is required, the process 900 can proceed directly to step 995. At 995, an updated medication list can be presented for the patient according to the approval. For example, when a new medication has been purchased from the pharmacy according to the updated prescription, the new medication can be added to the list. The medication that the prescription replaced can be removed from the consolidated medication list. The patient can be asked to verify that the patient has discontinued the removed medication.

Figure 10:
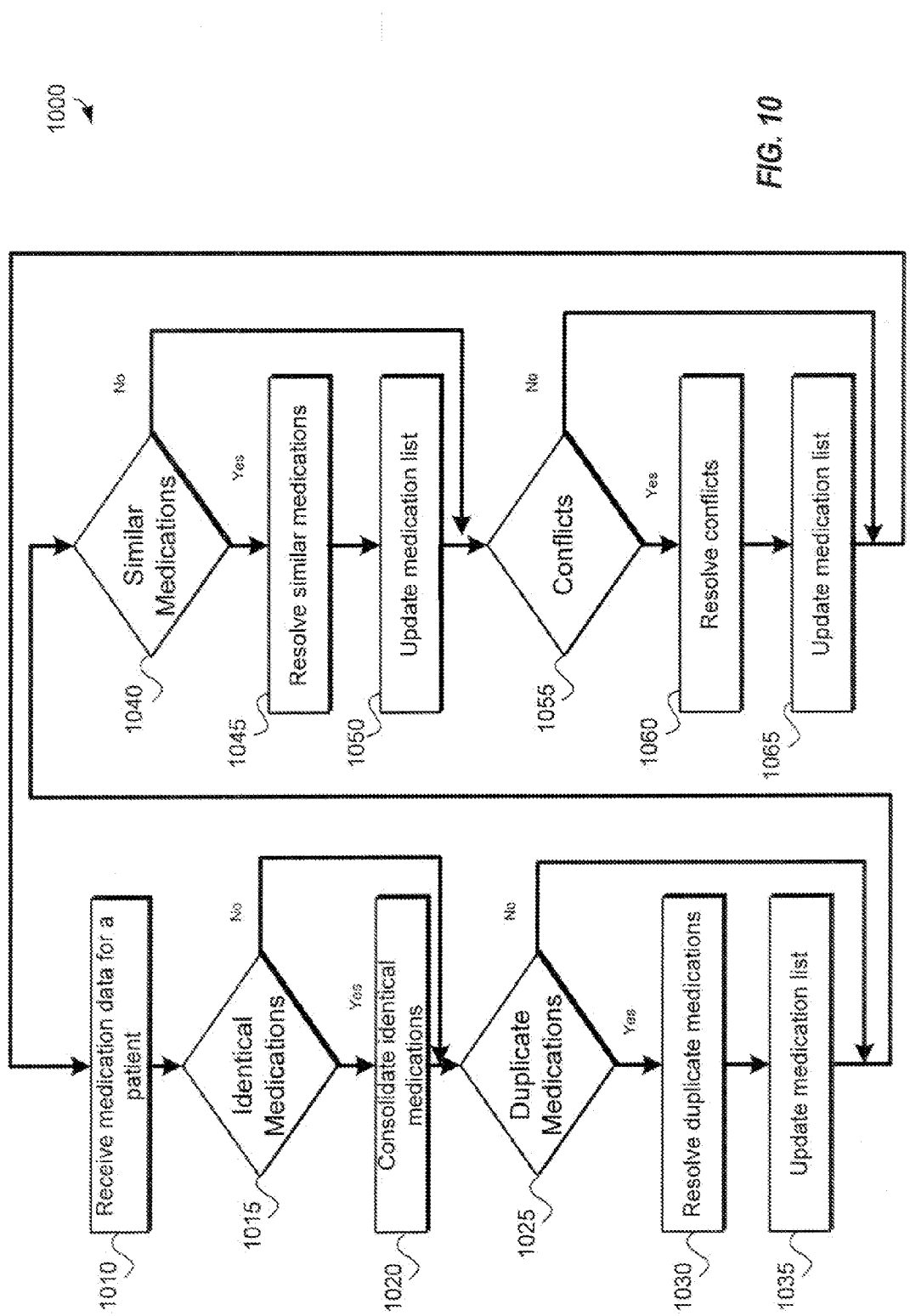
FIG. 10 shows an example process for maintaining an updated a patient medication list.

FIG. 10 shows an example process 1000 for maintaining an updated a patient medication list. At 1010, the process 1000 receives medication data for a patient which can be compiled into a medication list. The medication data can be obtained from multiple sources and can include entries for multiple medications. The medication data can include claims data for prescription medications, prescription data regarding prescriptions written or ordered, or medication data entered by the patient. At 1015, the process 1000 can determine whether the medication data contains entries for identical medications. If there are entries for identical medications, then the process consolidates 1020 the entries for identical medications. If there are no identical entries, the process 1000 moves to step 1025. At 1025, the process 1000 identifies whether there are entries for duplicate medications. If there are duplicate medications, the process 1000 resolves at 1030 duplicate medications. The resolution can include the patient identifying whether the patient is currently taking the duplicate medications. The resolution can include a physician providing a resolution over a network, such as discontinuing a medication, adding a new prescription etc. When a resolution is received, the medication list is updated 1035 according to the resolution.

At 1040, the process 1000 determines whether there are entries in the medication list for similar medications. If there are similar medications, the similar medications are resolved at 1045. The process 1000 can resolve the similar medications by receiving patient input that the patient is not currently taking all of the similar medications. In some examples, the resolution can include receiving a resolution from a physician over a network, such as discontinuing a medication, adding a new prescription etc. When a resolution is received, the medication list is updated 1050 according to the resolution.

At 1055, the process 1000 determines whether there are conflicts in the medication list. If there are conflicts, the conflicts are resolved at 1060. The process can resolve conflicts with a physician over a network. When a resolution is received, such as discontinuing a medication, adding a new prescription, etc, the medication list is updated 1065 according to the resolution.

The process 1000 can return to step 1010 where additional medication data can be received. The process 1000 can be repeated with the additional medication data to maintain an updated the medication list. For example, when additional data related to additional prescriptions are received for a patient from one or more sources, the process 1000 can identify 1015 if the data contain entries for identical medications, and can identify if the additional medical data contain identical entries with medication already on the medication list or already removed from the medication list. If so, then the identical medications entries can be consolidated at 1020. If not, then the process 1000 can continue to determine whether the medication data contains duplicate medications 1025, similar medications 1040, conflicts 1055 in the additional medical data and medication data already on the medication list. The medication list can be updated accordingly.

In some examples, the process 1000 can be performed in a different order than listed in FIG. 10. For example, the update the medication list steps 1035, 1045, and 1065 can be performed as one step or can be performed as duplicate medications are resolved 1030, similar medications are resolved 1045, and conflicts are resolved 1060 and not necessarily in that order.

Figure 11:
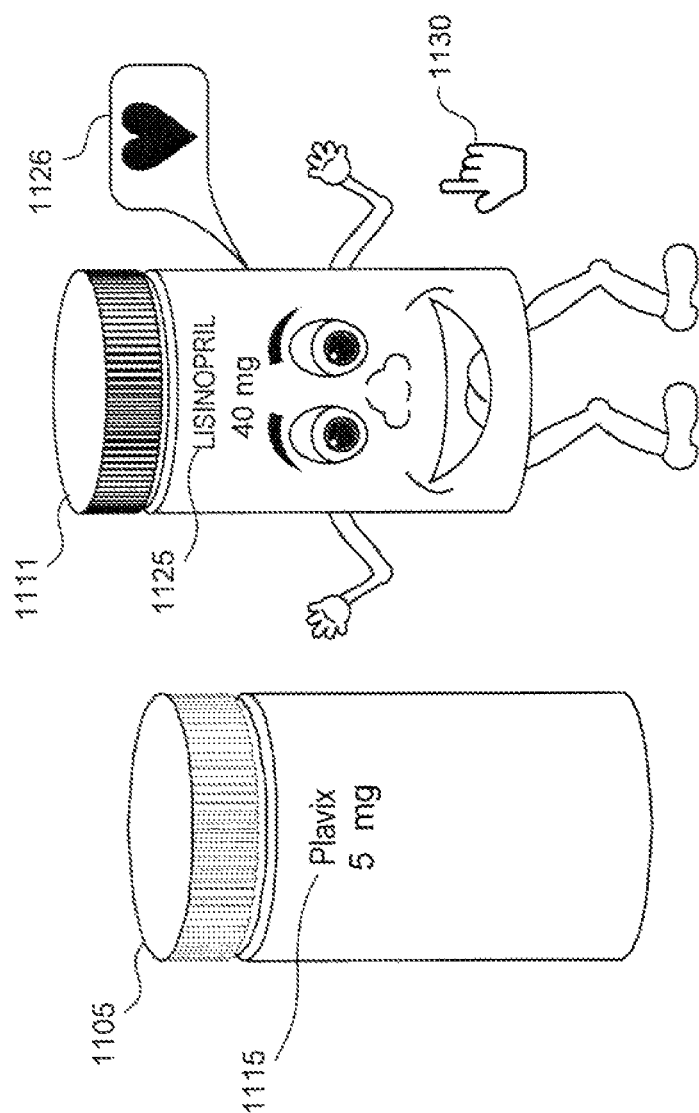
FIG. 11 shows example medication bottles for displaying medications in a medication list.

An interactive patient medication list can also be presented to the patient with the medications depicted in medication container such as medication bottles similar to those the patient has received from his/her pharmacy. FIG. 11 shows example medication bottles for displaying medications in a medication list, including a first bottle 1105 of Plavix in 5 mg tablets and a second bottle 1111 of Lisinopril 40 mg. The second bottle 1111 is stylized with human characteristics and has an indicator 1126 showing that the medication is categorized as a heart medication. These bottles can be user selectable to invoke various functionality such as to display more information regarding the medication, the prescription, the dosage, etc. The bottles can also be moved such as by clicking and dragging with pointer 1130. Other medication containers can be depicted in a graphical user-interface such as containers for other routes of administration such as a syringe for injectable medications, oral or nasal aerosol canisters, tubes for topical ointments and other delivery systems.

FIG. 12a shows an example of an interactive patient medication list 1200. The interactive patient medication list includes multiple medications. The multiple medications in the list can be compiled from medication data received from multiple sources. Identical medications can be consolidated on the list. The multiple medications from the consolidated patient medication list are shown in an interactive graphical format in the form of medication bottles, such as those the patient would receive from the patient's pharmacy. Exemplary bottle 1203 has a label 1204 with medication data for one of the medications on the patient medication list: SERTRALINE HCL 100 MG TAB. The label can also include other medication data such as frequency the medication should be taken (frequency of administration).

The medication list 1200 is shown with a medicine cabinet 1215. The medicine cabinet 1215 has a horizontal dimension demarcated by shelves and a vertical dimension demarcated by columns. Each of the shelves can indicate a drug category. For example, the medicine cabinet 1215 has a first shelf 1223 for the drug category "brain and pain", a second shelf 1225 for the drug category "heart and lung", a third shelf 1227 for the drug category "stomach and digestion", a fourth shelf 1229 for the drug category "sugar, fat, and blood", and a fifth shelf 1231 for the drug category "infection". The columns indicate the dosing characteristics, such as frequency of dosing. For example, the medicine cabinet 1215 has a first column 1217 for medications that should be taken three times a day, a second column 1219 for medications that should be taken once a day, and a third column 1221 for medications that should be taken once a week.

In some implementations, the number of columns and the characteristics of the columns may differ from the above example. For example, the first column can contain medications that are to be taken once a day; the second column can contain medications that are to be taken twice a day; the third column may contain medications that are to be taken three times a day; a fourth column can contain medications that are to be taken more than three times a day; the fifth column can contain medications that are taken on as "as-needed" basis regardless of frequency; and the sixth column can contain all others or those with unknown frequencies of dosing based on available information.

The medications can be moved into and organized in the medication cabinet 1215. The bottles representing the multiple medications on the patient medication list are interactive. For example, the bottles can be moved. The patient can move the bottles, e.g., using a pointer 1230, into the medicine cabinet 1215. The medicine cabinet can be configured to only receive medications into locations in the cabinet that match the drug category (horizontal dimension) and/or the frequency of administration (vertical dimension). Otherwise, the patient medication list can be configured to pop a medication bottle back out of the cabinet when the patient attempts to put the medication bottle in the incorrect location.

Figure 12B:
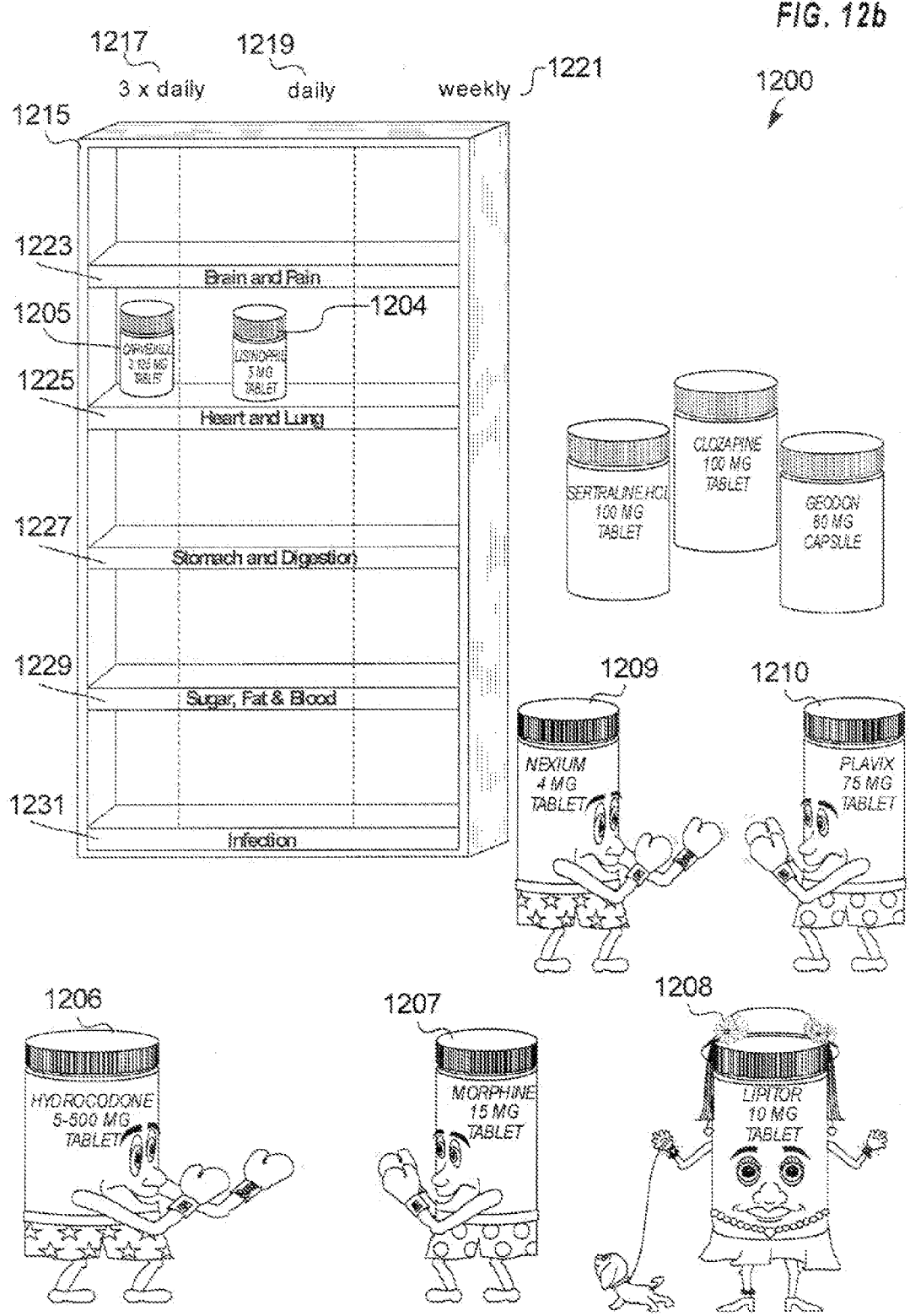

FIG. 12b shows two of the medication bottles 1204 and 1205 moved into locations in the medicine cabinet 1215. The medication bottle 1204 for lisinopril is a heart and lung medication and therefore was accepted into shelf 1225. The prescription for lisinopril also indicates that the medication should be taken once a day. Accordingly, the medication bottle 1204 was accepted into the second column 1219. The medication bottle 1205 for carvedilol is also a heart and lung medication and therefore was also accepted into shelf 1225. The prescription for carvedilol indicates that the medication should be taken three times a day and therefore was accepted into the first column 1217.

Figure 12D:
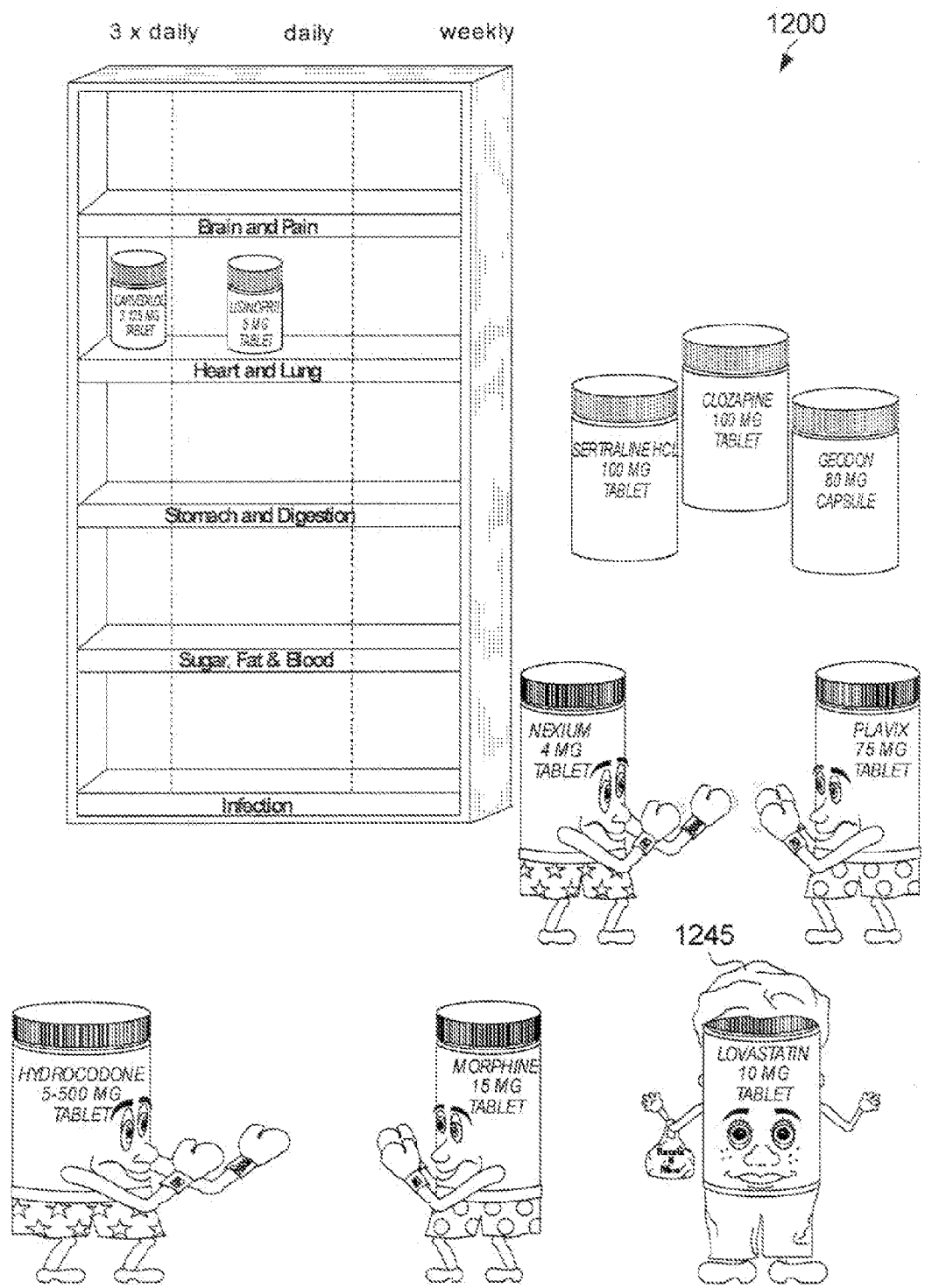

Cost savings changes can be determined and depicted for medications on the medication list 1200. For example, in FIG. 12c, a medication on the medication list 1200 is depicted as a medication bottle 1208 wearing costly apparel, indicating that a cost savings change for the medication has been determined. The medication bottle 1208 is for the medication Lipitor. By selecting the medication bottle 1208, e.g. using pointer 1230, a request is sent for the cost savings change. The request can be sent to a health care professional such as the patient's physician. When the change has been requested the bottle 1208 can change into a bottle 1245 as shown in FIG. 12d. The bottle 1245 is for the cost savings change, in this example, the medication lovastatin. The bottle 1245 is depicted as an economical shopper instead of wearing costly apparel.

In some examples, the bottle 1208 can change into a bottle 1245 when the prescription has been filled, indicating that the cost savings has been realized. In the meantime between the request for the cost savings change and the prescription being filled, an indication can be shown that provides a status of the request for the cost savings alternative. For example, an indicator can be presented with bottle 1208 that indicates "request pending." When a user moves a mouse or pointer over the "request pending" indicator, a more detail status update can be presented. In some examples, medication bottle depictions requiring some intervention may change to a "glowing" state, indicated by a color change and surrounding hue.

Figure 12E:
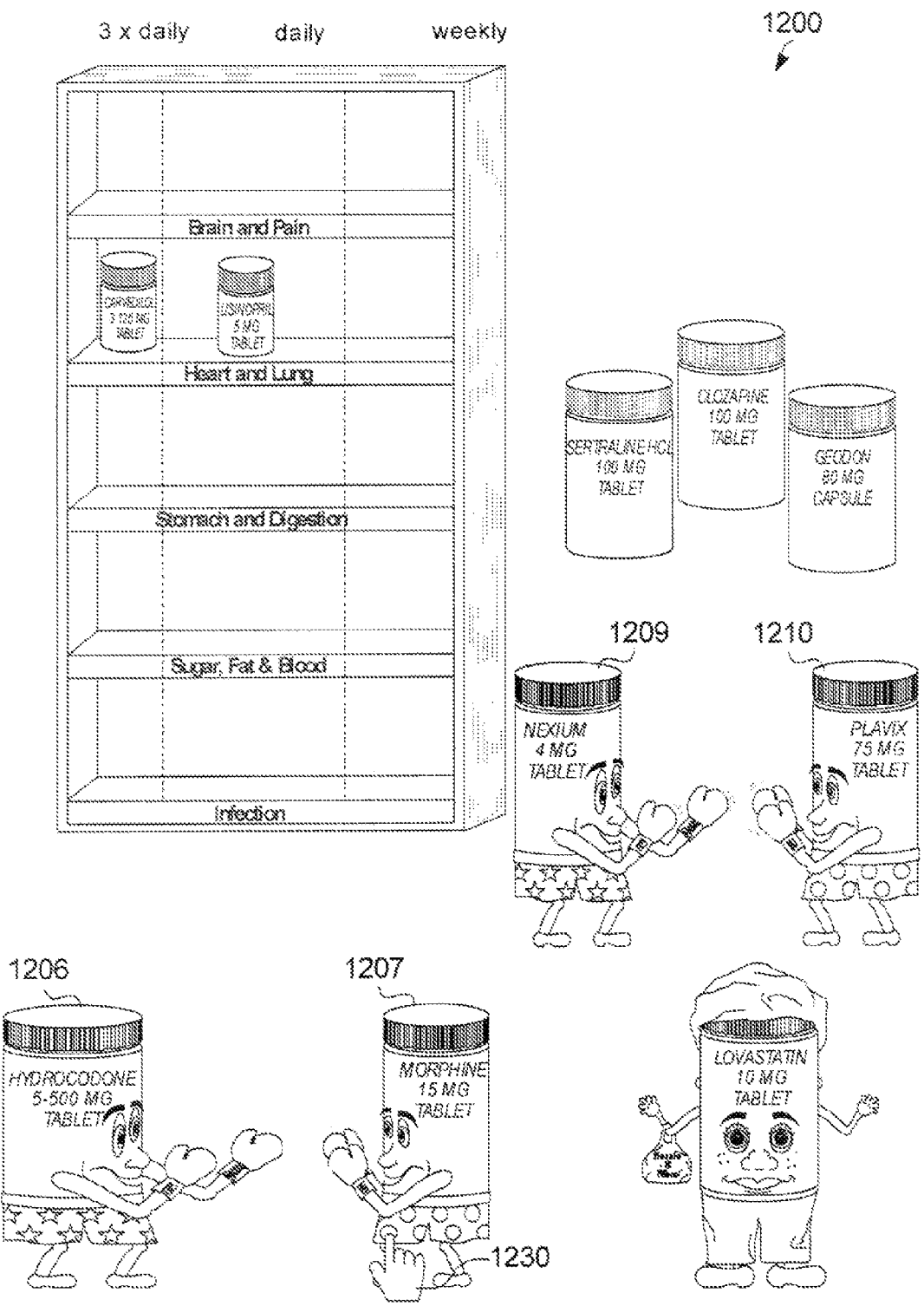

Problems on the patient medication list can be determined and depicted on the medication list 1200. For example, as shown in FIG. 12e, medications determined to be conflicting medications can be shown in physical conflict. For example, bottles 1209 and 1210 for Nexium and Plavix respectively are shown in conflict because Nexium and Plavix were determined to be potentially conflicting medications. The conflicting medications can be an image of the bottles conflicting or an animation of the bottles conflicting. Also, bottles 1206 and 1207 for hydrocodone and morphine are shown in conflict because hydrocodone and morphine were determined to be therapeutic duplicates. Information regarding the conflict between hydrocodone and morphine can be presented in the user interface 1200, for example, when the pointer 1230 moves over a region associated with the bottles 1206 and 1207.

The patient can provide input requesting an identified problem be resolved. For example, the patient can select the conflicting medication bottles 1206 and 1207 using pointer 1230 as shown in FIG. 12e. The request can be sent to a health care professional such as the patient's physician. While the conflict is being resolved by the health care professional, the medication list 1200 can show the resolution of the conflict between medications shown as bottles 1206 and 1207 as pending 1259 in FIG. 12f.

Figure 12G:
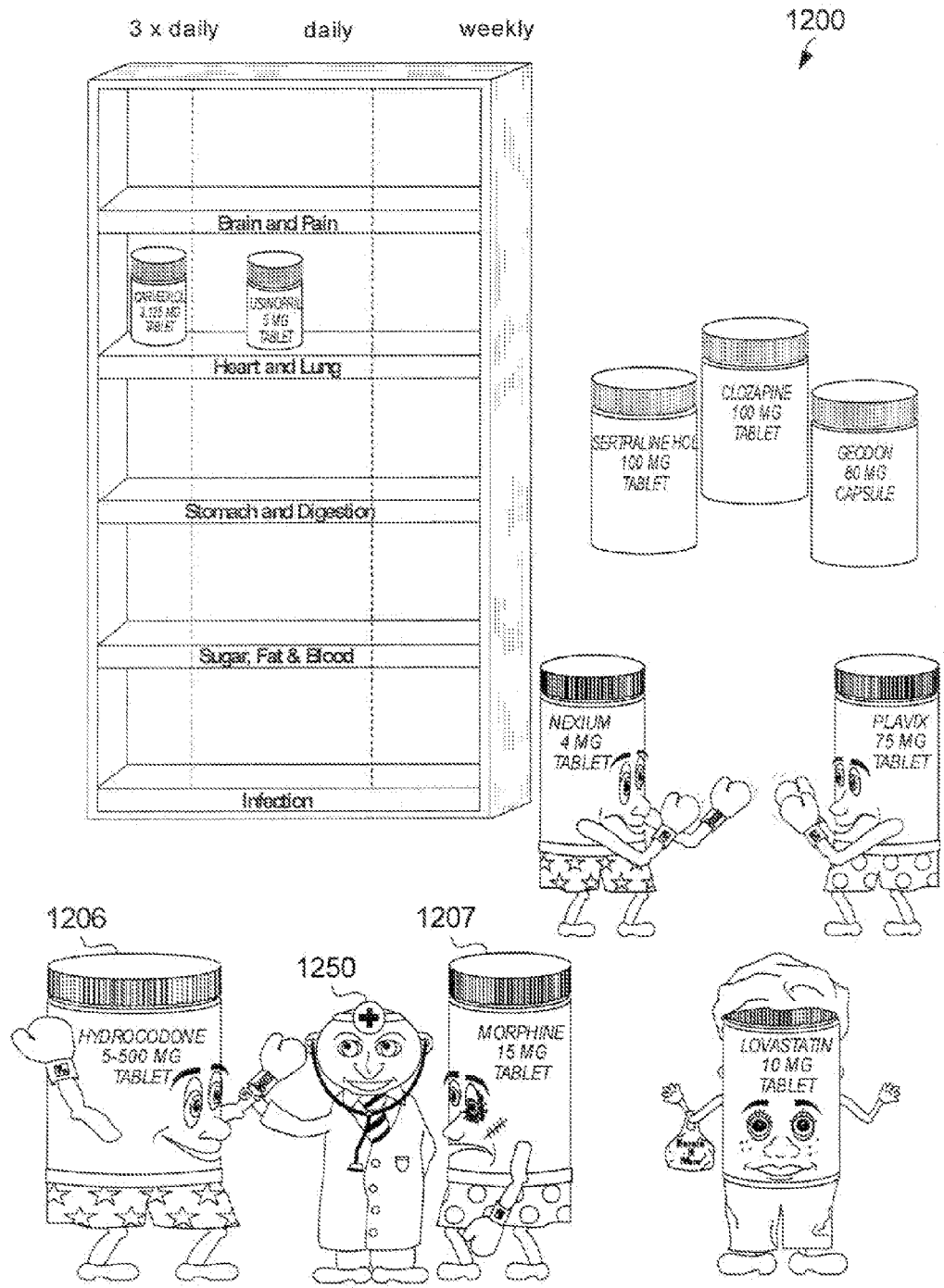

When the health care professional provides a resolution, the medication list can be updated. The update, for example as shown in FIG. 12g, can be depicted with one of the medication bottles as a winner. The bottle 1206 for medication hydrocodone is declared the winner by a graphical depiction 1250 of a physician. The patient can provide user input indicating that the patient has discontinued the losing medication corresponding to bottle 1207. The medication list 1200 can be updated with the bottle 1207 for the losing medication being removed from the list 1200. In some examples, the health care professional can determine that no change should be made and both bottles 1206 and 1207 are declared winners. Once a container of medication is declared the "loser," instructions for the proper discarding of the medications in a safe and environmentally-sound way can be presented to the user in the form of a balloon over the animated bottle. The bottle can assume a slumped-over, exhausted posture at the same time. Following acknowledgment of the instructions, the medication bottle can disappear with an animation depicting a "pop" and appropriate sound accompanying the animation.

Figure 12H:
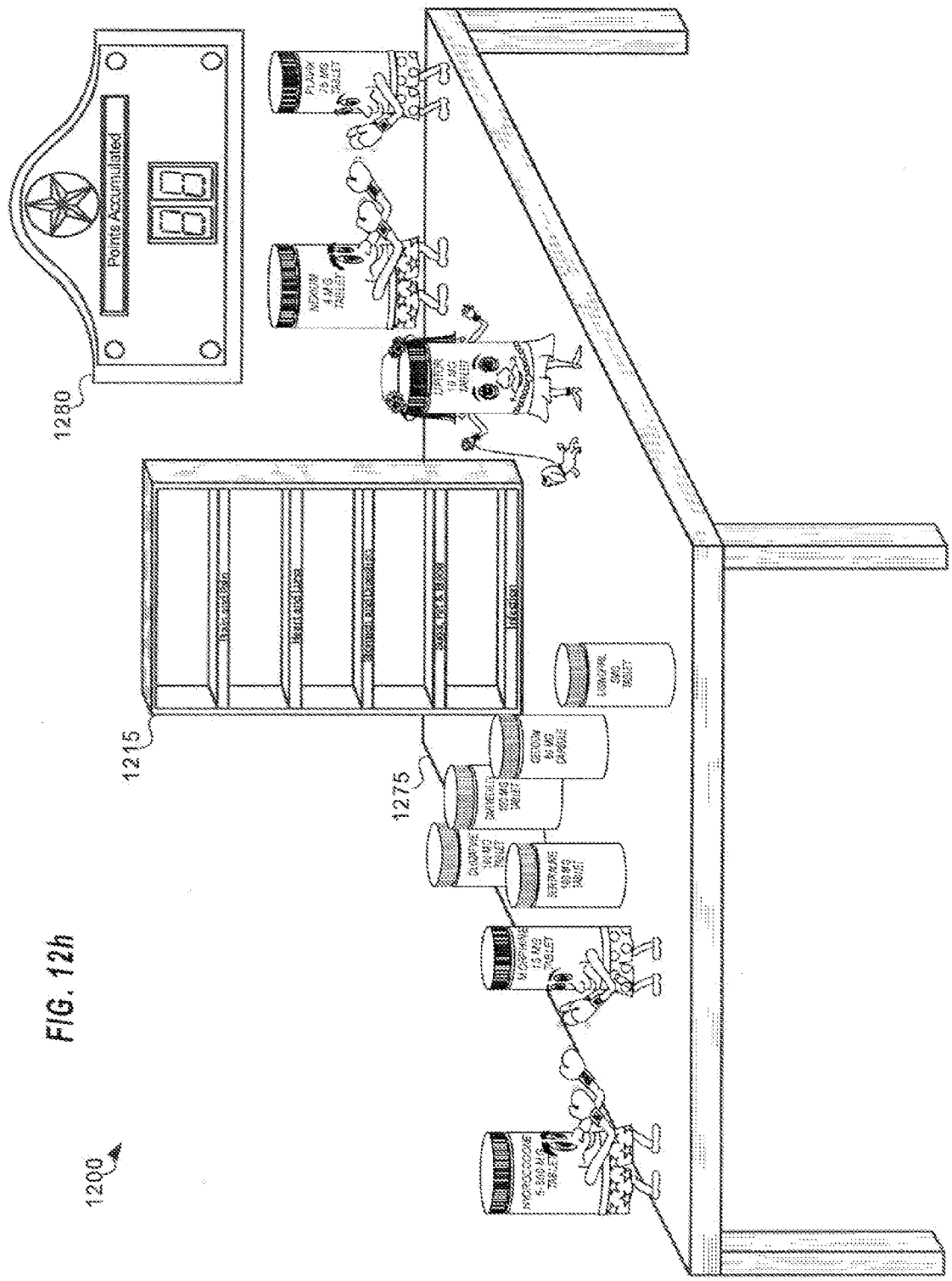

FIG. 12h shows a depiction of the interactive medication list 1200 with the multiple medication bottles and the medication cabinet 1215 on a table 1275. The medication list 1200 includes a point counter 1280 for depicting points that are accumulated as the patient interacts with the medication list 1200 to resolve problems in the medication list, to request cost savings, and/or as the patient organizes the medications in the medication cabinet 1215 according to drug category and frequency of administration. Points can also accumulate as the patient is adherent to the patient's medication regime. In some implementations, the patient can later redeem the points for prizes.

In some implementations, the vertical dimension of the medication cabinet 1215 can indicate drug categories and the horizontal dimension can indicate frequency of administration. The vertical and/or horizontal dimension of the medication cabinet can also can also indicate other dosing characteristics such as route of administration, duration of administration, type of delivery system, size of dose (e.g. 1 pill per dose, 2 pills per dose, etc.) amount of dose, days of week the medication is to be taken etc.

In some implementations, multiple medication cabinets can be displayed. Each medication cabinet can be for a different category of drug or different dosing characteristic. The multiple medication cabinets can be configured to receive only medications corresponding to the respective medication cabinet's corresponding drug category or dosing characteristic. Also, other receptacles can be used for organizing the patient's medications such as a bag or bags, box, pill box and the like.

Embodiments of the subject matter and the operations described in this document can be implemented in digital electronic circuitry, or in computer software, firmware, or hardware, including the structures disclosed in this document and their structural equivalents, or in combinations of one or more of them. Embodiments of the subject matter described in this document can be implemented as one or more computer programs, i.e., one or more modules of computer program instructions, encoded on a computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this document can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this document can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this document can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this document can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this document, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), peer-to-peer networks (e.g., ad hoc peer-to-peer networks), wireless networks, mobile phone networks etc.

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Particular implementations have been described in this document. Variations and enhancements of the described implementations and other implementations can be made based on what is described and illustrated in this document. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer implemented method comprising:
   displaying, by a computer system in a graphical user-interface, movable depictions of medication containers for medications in an interactive list of medications for a patient, each medication container having a corresponding medication category;
   displaying, by the computer system in the graphical user-interface, a depiction of a medicine cabinet for organizing the medications, wherein the depiction of the medicine cabinet comprises multiple shelves that have corresponding medication categories, each of the shelves configured to hold one or more of the movable depictions of medication containers;
   receiving, by the computer system, first patient input moving a movable depiction of a first medication container from among the movable depictions of medication containers to a correct first location of the depiction of the medicine cabinet, wherein the first location is correct because a medication category of the first location matches a medication category associated with the first medication container;
   holding, by the computer system in the graphical user-interface, the movable depiction of the first medication container in the depiction of the medicine cabinet at the first correct location where the movable depiction of the first medication container was dragged;
   receiving, by the computer system, second patient input moving a movable depiction of a second medication container from among the movable depictions of medication containers to an incorrect second location of the depiction of the medicine cabinet; and
   popping, by the computer system in the graphical user-interface, movable depiction of the second medication container back out of the depiction of the medicine cabinet from the incorrect second location where the movable depiction of the second medication container was dragged, wherein the moveable depictions of the medication containers are stylized to have human characterisitics.

2. The method of claim 1, wherein
   the medications have corresponding frequencies of administration;
   the depiction of the medicine cabinet has columns that correspond to frequency of administration; and
   the first location is correct because, in addition to the medication category of the first location matching the medication category of the first medication container, a frequency of administration of the first location also matches a frequency of administration of the first medication container.

3. The method of claim 1, wherein
   the medications have corresponding dosing characteristics;
   the depiction of the medicine cabinet has columns that correspond to dosing characteristics; and
   the first location is correct because, in addition to the medication category of the first location matching the medication category of the first medication container, a dosing characteristic of the first location also matches a dosing characteristic of the first medication container.

4. The method of claim 1, further comprising adding, by the computer system, credit to an incentive program for the patient in response to the receiving the first patient input, wherein the credit can be redeemed for a prize.

5. The method of claim 1, wherein the human stylized movable medication container depictions are of bottles having labels depicting prescription data for the medications and the stylized human characteristics include an indicator corresponding to the category.

6. A non-transitory computer readable medium encoded with instructions that when executed by a data processing apparatus cause the data processing apparatus to perform operations comprising:
 displaying, in a graphical user-interface, movable depictions of medication containers for medications in an interactive list of medications for a patient, each medication container having a corresponding medication category;
 displaying, in the graphical user-interface, a depiction of a medicine cabinet for organizing the medications, wherein the depiction of the medicine cabinet comprises multiple shelves that have corresponding medication categories, each of the shelves configured to hold one or more of the movable depictions of medication containers;
 receiving first patient input moving a movable depiction of a first medication container from among the movable depictions of medication containers to a correct first location of the depiction of the medicine cabinet, wherein the first location is correct because a medication category of the first location matches a medication category associated with the first medication container;
 holding, in the graphical user-interface, the movable depiction of the first medication container in the depiction of the medicine cabinet at the first correct location where the movable depiction of the first medication container was dragged;
 receiving second patient input moving a movable depiction of a second medication container from among the movable depictions of medication containers to an incorrect second location of the depiction of the medicine cabinet; and
 popping, in the graphical user-interface, the movable depiction of the second medication container back out of the depiction of the medicine cabinet from the incorrect second location where the movable depiction of the second medication container was dragged, wherein the moveable depictions of the medication containers are stylized to have human characterisitics.

7. The non-transitory computer readable medium of claim 6 wherein
 the medications have corresponding frequencies of administration;
 the depiction of the medicine cabinet has columns that correspond to frequency of administration; and
 the first location is correct because, in addition to the medication category of the first location matching the medication category of the first medication container, a frequency of administration of the first location also matches a frequency of administration of the first medication container.

8. The non-transitory computer readable medium of claim 6, wherein
 the medications have corresponding dosing characteristics;
 the depiction of the medicine cabinet has columns that correspond to dosing characteristics; and
 the first location is correct because, in addition to the medication category of the first location matching the medication category of the first medication container, a dosing characteristic of the first location also matches a dosing characteristic of the first medication container.

9. The non-transitory computer readable medium of claim 6, wherein the instructions when executed by the data processing apparatus cause the data processing apparatus to perform operations further comprising:
 adding credit to an incentive program for the patient in response to the receiving the first patient input, wherein the credit can be redeemed for a prize.

10. The non-transitory computer readable medium of claim 6, wherein human stylized movable medication container depictions are of bottles having labels depicting prescription data for the medications and the stylized human characteristics include an indicator corresponding to the category.

11. A system comprising:
 a data storage device for storing medication data received from multiple sources over one or more networks;
 a computing system including processor electronics configured to perform operations comprising:
  displaying, in a graphical user-interface, movable depictions of medication containers for medications in an interactive list of medications for a patient, each medication container having a corresponding medication category;
  displaying, in the graphical user-interface, a depiction of a medicine cabinet for organizing the medications, wherein the depiction of the medicine cabinet comprises multiple shelves that have corresponding medication categories, each of the shelves configured to hold one or more of the movable depictions of medication containers; and
 receiving first patient input moving a movable depiction of a first medication container from among the movable depictions of medication containers to a correct first location of the depiction of the medicine cabinet, wherein the first location is correct because a medication category of the first location matches a medication category associated with the first medication container;
 holding, in the graphical user-interface, the movable depiction of the first medication container in the depiction of the medicine cabinet at the first correct location where the movable depiction of the first medication container was dragged;
 receiving second patient input moving a movable depiction of a second medication container from among the movable depictions of medication containers to an incorrect second location of the depiction of the medicine cabinet; and
 popping, in the graphical user-interface, the movable depiction of the second medication container back out of the depiction of the medicine cabinet from the incorrect second location where the movable depiction of the second medication container was dragged, wherein the moveable depictions of the medication containers are stylized to have human characterisitics.

12. The system of claim 11, wherein
 the medications have corresponding frequencies of administration;
 the depiction of the medicine cabinet has columns that correspond to frequency of administration; and
 the first location is correct because, in addition to the medication category of the first location matching the medication category of the first medication container, a frequency of administration of the first location also matches a frequency of administration of the first medication container.

13. The system of claim 11, wherein
the medications have corresponding dosing characteristics;
the depiction of the medicine cabinet has columns that correspond to dosing characteristics; and
the first location is correct because, in addition to the medication category of the first location matching the medication category of the first medication container, a dosing characteristic of the first location also matches a dosing characteristic of the first medication container.

14. The system of claim 11, wherein the processor electronics are further configured to perform the operations comprising adding credit to an incentive program for the patient in response to the receiving the first patient input, wherein the credit can be redeemed for a prize.

15. The system of claim 11, wherein human stylized movable medication container depictions are of bottles having labels depicting prescription data for the medications and the stylized human characteristics include an indicator corresponding to the category.

* * * * *

UNITED STATES PATENT AND TRADEMARK OFFICE
CERTIFICATE OF CORRECTION

PATENT NO. : 8,494,880 B2
APPLICATION NO. : 13/011783
DATED : July 23, 2013
INVENTOR(S) : Louis Christopher Tripoli It is certified that error appears in the above-identified patent and that said Letters Patent is hereby corrected as shown below:

In the Claims

Claim 1, Column 24, line 42, after "interface", insert -- the --.

Claim 1, Column 24, lines 47-48, delete "characterisitics." and insert -- characteristics. -- therefor.

Claim 6, Column 25, line 51, delete "characterisitics." and insert -- characteristics. -- therefor.

Claim 10, Column 26, line 16, after "wherein" insert -- the --.

Claim 11, Column 26, line 60, delete "characterisitics." and insert -- characteristics. -- therefor.

Claim 15, Column 27, line 20, after "wherein" insert -- the --.

Signed and Sealed this
First Day of October, 2013

Teresa Stanek Rea
*Deputy Director of the United States Patent and Trademark Office*